(12) United States Patent
Singh et al.

(10) Patent No.: US 8,242,131 B2
(45) Date of Patent: Aug. 14, 2012

(54) METHODS OF TREATING MIDDLE-OF-THE-NIGHT INSOMNIA

(75) Inventors: Nikhilesh Singh, Mill Valley, CA (US); Sathasivan Indiran Pather, Greenbrae, CA (US)

(73) Assignee: Transcept Pharmaceuticals, Inc., Pt. Richmond, CA (US)

( * ) Notice: Subject to any disclaimer, the term of this patent is extended or adjusted under 35 U.S.C. 154(b) by 1185 days.

(21) Appl. No.: 11/439,874

(22) Filed: May 23, 2006

(65) Prior Publication Data

US 2007/0066643 A1 Mar. 22, 2007

Related U.S. Application Data

(60) Provisional application No. 60/684,842, filed on May 25, 2005, provisional application No. 60/741,673, filed on Dec. 1, 2005, provisional application No. 60/788,340, filed on Mar. 31, 2006, provisional application No. 60/788,249, filed on Mar. 31, 2006.

(51) Int. Cl.
*A61K 31/44* (2006.01)

(52) U.S. Cl. .................. 514/294; 514/923

(58) Field of Classification Search .......... 514/294, 514/923

See application file for complete search history.

(56) References Cited

U.S. PATENT DOCUMENTS

| | | |
|---|---|---|
| 4,382,938 A | 5/1983 | Kaplan et al. |
| 4,405,647 A | 9/1983 | Fisher et al. |
| 4,460,592 A | 7/1984 | Kaplan et al. |
| 4,808,594 A | 2/1989 | George et al. |
| 4,863,737 A | 9/1989 | Stanley et al. |
| 5,178,867 A | 1/1993 | Guittard et al. |
| 5,178,878 A | 1/1993 | Wehling et al. |
| 5,223,264 A | 6/1993 | Wehling et al. |
| 5,284,659 A | 2/1994 | Cherukuri et al. |
| 5,288,497 A | 2/1994 | Stanley et al. |
| 5,288,498 A | 2/1994 | Stanley et al. |
| 5,503,846 A | 4/1996 | Wehling et al. |
| 5,576,014 A | 11/1996 | Mizumoto |
| 5,686,094 A | 11/1997 | Acharya |
| 5,719,197 A | 2/1998 | Kanios et al. |
| 5,785,989 A | 7/1998 | Stanley et al. |
| 5,855,908 A | 1/1999 | Stanley et al. |
| 5,869,082 A | 2/1999 | Dugger, III |
| 5,895,664 A | 4/1999 | Cherukuri et al. |
| 5,955,098 A | 9/1999 | Dugger, III |
| 5,965,162 A | 10/1999 | Fuisz et al. |
| 6,024,981 A | 2/2000 | Khankari et al. |
| 6,110,486 A | 8/2000 | Dugger, III |
| 6,197,334 B1 | 3/2001 | Renda |
| 6,200,604 B1 | 3/2001 | Pather et al. |
| 6,210,699 B1 | 4/2001 | Acharya et al. |
| 6,211,392 B1 | 4/2001 | Fang et al. |
| 6,218,397 B1 | 4/2001 | Chen |
| 6,242,460 B1 | 6/2001 | Ettema et al. |
| 6,264,981 B1 | 7/2001 | Zhang et al. |
| 6,264,987 B1 | 7/2001 | Wright et al. |
| 6,280,770 B1 | 8/2001 | Pather et al. |
| 6,344,222 B1 | 2/2002 | Cherukuri et al. |
| 6,348,485 B1 | 2/2002 | Ohkawa et al. |
| 6,350,470 B1 | 2/2002 | Pather et al. |
| 6,358,060 B2 | 3/2002 | Pinney et al. |
| 6,368,625 B1 | 4/2002 | Siebert et al. |
| 6,383,471 B1 | 5/2002 | Chen et al. |
| 6,391,335 B1 | 5/2002 | Pather et al. |
| 6,441,018 B2 | 8/2002 | Faraci et al. |
| 6,509,036 B2 | 1/2003 | Pather et al. |
| 6,514,531 B1 | 2/2003 | Alaux et al. |
| 6,569,463 B2 | 5/2003 | Patel et al. |
| 6,576,250 B1 | 6/2003 | Pather et al. |
| 6,586,478 B2 | 7/2003 | Ackman et al. |
| 6,589,556 B2 | 7/2003 | Cherukuri |
| 6,624,162 B2 | 9/2003 | Uchida et al. |
| 6,638,535 B2 | 10/2003 | Lemmens et al. |
| 6,645,528 B1 | 11/2003 | Straub |
| 6,656,492 B2 | 12/2003 | Kajiyama |
| 6,676,931 B2 | 1/2004 | Dugger, III |
| 6,692,771 B2 | 2/2004 | Pather et al. |
| 6,720,001 B2 | 4/2004 | Chen et al. |
| 6,733,781 B2 | 5/2004 | Abu-Izza |
| 6,753,011 B2 | 6/2004 | Faour |
| 6,759,059 B1 | 7/2004 | Pettersson et al. |
| 6,761,910 B1 | 7/2004 | Pettersson et al. |
| 6,893,654 B2 | 5/2005 | Pinney et al. |
| 6,923,988 B2 | 8/2005 | Patel |
| 6,969,508 B2 | 11/2005 | Dugger, III |
| 6,977,070 B2 | 12/2005 | Dugger, III |
| 6,998,110 B2 | 2/2006 | Dugger, III |
| 7,118,765 B2 | 10/2006 | Norman |

(Continued)

FOREIGN PATENT DOCUMENTS

WO WO 99/16417 4/1999

(Continued)

OTHER PUBLICATIONS

Rouhi et al. The Right Stuff. Chemical Engineering and News. Feb. 2003. pp. 32-35.*
"Ambien® (zolpidem tartrate)" Sanofi-Synthelabo, Inc. ZPSS-5A (Jun. 2002).
Avdeef, A. "Physiochemical Profiling (Solubility, Permeability and Charge State)." Current Topics in Medicinal Chemistry vol. 1 No. 4: 277-351 (2001).
Danjou, P. et al., "A comparison of the residual effects of zaleplon and zolpidem following administration 5 to 2 hours before awakening." Br. J. Clin. Pharmacology 48:367-374 (Jun. 1999).
Doghramji, K. "The Need for Flexibility in Dosing of Hypnotic Agents." Sleep 23 (Supplement 1): S16-S20 (2000).
Fry, J. et al., "Zaleplon improves sleep without producing rebound effects in outpatients with insomnia." International Clinical Pharmacology 15(3): 141-152 (2000).

(Continued)

*Primary Examiner* — Renee Claytor
(74) *Attorney, Agent, or Firm* — O'Melveny & Myers LLP

(57) ABSTRACT

The present invention provides compositions and methods for treating middle-of-the-night insomnia without residual sedative effects upon awakening by administering low doses (about 5 mg or less) of zolpidem or a salt thereof.

25 Claims, 7 Drawing Sheets

U.S. PATENT DOCUMENTS

| | | | |
|---|---|---|---|
| 7,163,705 | B2 | 1/2007 | Johnson et al. |
| 7,658,945 | B2 | 2/2010 | Singh |
| 7,682,628 | B2 | 3/2010 | Singh |
| 2001/0051186 | A1 | 12/2001 | Acharya et al. |
| 2002/0077332 | A1 | 6/2002 | Aronhime |
| 2002/0098264 | A1 | 7/2002 | Cherukuri et al. |
| 2003/0077227 | A1 | 4/2003 | Dugger |
| 2003/0077228 | A1 | 4/2003 | Dugger, III |
| 2003/0077229 | A1 | 4/2003 | Dugger, III |
| 2003/0082107 | A1 | 5/2003 | Dugger, III |
| 2003/0091629 | A1 | 5/2003 | Pather et al. |
| 2003/0095925 | A1 | 5/2003 | Dugger, III |
| 2003/0095926 | A1 | 5/2003 | Dugger, III |
| 2003/0095927 | A1 | 5/2003 | Dugger, III |
| 2003/0124184 | A1 | 7/2003 | Mezaache et al. |
| 2003/0185761 | A1 | 10/2003 | Dugger, III |
| 2003/0185884 | A1 | 10/2003 | Singh et al. |
| 2003/0190286 | A1 | 10/2003 | Dugger, III |
| 2003/0211047 | A1 | 11/2003 | Dugger, III |
| 2003/0232080 | A1 | 12/2003 | Pather et al. |
| 2004/0062716 | A1 | 4/2004 | Dugger, III |
| 2004/0109890 | A1 | 6/2004 | Sugimoto |
| 2004/0120895 | A1 | 6/2004 | Dugger |
| 2004/0136914 | A1 | 7/2004 | Dugger, III |
| 2004/0136915 | A1 | 7/2004 | Dugger, III |
| 2004/0141923 | A1 | 7/2004 | Dugger et al. |
| 2004/0185097 | A1 | 9/2004 | Kannan et al. |
| 2004/0213855 | A1 | 10/2004 | Pettersson |
| 2004/0258750 | A1 | 12/2004 | Alaux et al. |
| 2004/0265239 | A1 | 12/2004 | Dugger et al. |
| 2004/0265375 | A1 | 12/2004 | Platteeuw et al. |
| 2005/0002867 | A1 | 1/2005 | Dugger et al. |
| 2005/0031677 | A1 | 2/2005 | Pather et al. |
| 2005/0037072 | A1 | 2/2005 | Pather et al. |
| 2005/0038042 | A1 | 2/2005 | Codd et al. |
| 2005/0142197 | A1 | 6/2005 | Moe |
| 2005/0142198 | A1 | 6/2005 | Moe |
| 2005/0147666 | A1 | 7/2005 | Ohta |
| 2005/0164987 | A1 | 7/2005 | Barberich |
| 2005/0226925 | A1 | 10/2005 | Singh |
| 2005/0281752 | A1 | 12/2005 | Dugger, III |
| 2006/0024365 | A1 | 2/2006 | Vaya et al. |
| 2006/0216352 | A1 | 9/2006 | Nystrom et al. |
| 2006/0276501 | A1 | 12/2006 | Singh |
| 2006/0281783 | A1 | 12/2006 | Singh |
| 2007/0037843 | A1 | 2/2007 | Aronhime |
| 2007/0066643 | A1 | 3/2007 | Singh |
| 2007/0123562 | A1 | 5/2007 | Singh |
| 2007/0225322 | A1 | 9/2007 | Singh |
| 2007/0287740 | A1 | 12/2007 | Singh |
| 2008/0008753 | A1 | 1/2008 | Singh et al. |
| 2008/0057119 | A1 | 3/2008 | Singh |
| 2008/0132517 | A1 | 6/2008 | Chow |
| 2008/0132535 | A1 | 6/2008 | Singh |
| 2008/0145425 | A1 | 6/2008 | Marija |
| 2008/0262025 | A1 | 10/2008 | Kumar |
| 2008/0287456 | A1 | 11/2008 | Roberts |
| 2008/0311208 | A1 | 12/2008 | Pettersson |
| 2010/0143486 | A1 | 6/2010 | Davar |
| 2010/0240695 | A1 | 9/2010 | Singh |
| 2010/0249178 | A1 | 9/2010 | Singh |
| 2010/0266682 | A1 | 10/2010 | Davar |
| 2010/0291004 | A1 | 11/2010 | Singh |
| 2011/0039881 | A1 | 2/2011 | Singh |

FOREIGN PATENT DOCUMENTS

| | | |
|---|---|---|
| WO | WO 99/63977 | 12/1999 |
| WO | WO 00/16750 | 3/2000 |
| WO | WO 00/33835 | 6/2000 |
| WO | WO 00/38649 | 7/2000 |
| WO | WO 01/89476 | 11/2001 |
| WO | WO 2004/091585 | 10/2004 |
| WO | WO 2005/010002 | 2/2005 |
| WO | WO 2005/032519 | 4/2005 |
| WO | WO 2005/079761 | 9/2005 |
| WO | WO 2006/046041 | 5/2006 |

OTHER PUBLICATIONS

Galey, W. et al., "The In Vitro Permeability of Skin and Buccal Mucosa to Selected Drugs and Tritiated Water." The Journal of Investigative Dermatology vol. 67, No. 6: 713-717 (1976).

Gandhi, R. et al., "Bioadhesion in Drug Delivery." Indian Journal of Pharmaceutical Sciences 50(3): 145-152 (May-Jun. 1988).

Greenblatt, D. et al., "Comparative kinetics and dynamics of zalepon, zolpidem, and placebo." Clinical Pharmacolology & Therapeutics vol. 64, No. 5: 553-561 (Nov. 1998).

Greenblatt, D. et al., "Kinetic and dynamic interaction study of zolpidem with ketoconazole, itraconazole, and fluconazole." Clinical Pharmacology & Therapeutics vol. 64, No. 661-671 (Dec. 1998).

Harris, D. et al., "Drug Delivery via the Mucous Membranes of the Oral Cavity." Journal of Pharmaceutical Sciences vol. 81, No. 1: 1-10 (Jan. 1992).

Hindmarch et al., "Comparison of the residual effects of zaleplon and zolpidem after administration during the night." European Neuropsychopharmacology 10(suppl. 3): s394 Abstract No. P.6.026 (Sep. 2000).

Hindmarch et al., "Residual effects of zaleplon and zolpidem following middle of the night administration five hours to one hour before awakening." Human Psychopharmacology 16:159-167 (2001).

Hoehns and Perry. "Zolpidem: A nonbenzodiazepine hypnotic for treatment of insomnia." Clin. Pharmacy 12: 814-28 (Nov. 1993).

Holm, K. et al., "Zolpidem: An update of its Pharmacology, Therapeutic Efficacy and Tolerabilty in the Treatment of Insomnia." Adis Drug Evaluation 59(4): 865-889 (Apr. 2000).

Kansy, M. et al., "Physiochemical High Throughput Screening: Parallel Artificial Membrane Permeation Assay in the Description of Passive Absorption Processes." Journal of Medicinal Chemistry vol. 41, No. 7: 1007-1010 (Mar. 1998).

Lader, M.H. "Implications of hypnotic flexibility on patterns of clinical use." UCP Supplement 116: 14-19 (Jan. 2001).

Merlotti, L. et al. "The Dose Effects of Zolpidem on the Sleep of Healthy Normals." J. Clinical Psychopharmacology 9(1): 9-14 (Feb. 1989).

Nail, S. et al., "Fundamentals of Freeze-Drying." in Development and Manufacture of Protein Pharmaceuticals. Ed. Steven L. Nail and Michael J. Akers, New York: Kluwer Academic/Plenum Publishers 281-360 (2002).

Patat et al., "EEG profile of intravenous zolpidem in healthy volunteers." Psychopharmacology 114:138-146 (1994).

Rathbone, M. et al., "The oral cavity as a site for systemic drug delivery." Advanced Drug Delivery Reviews 13: 1-22 (1994).

Roth et al., "Daytime pharmacodynamic and pharmacokinetic evaluation of low-dose sublingual transmucosal zolpidem hemitartrate." Hum. Psychopharmacol. Clin. Exp. 23: 13-20 (2008).

Roth et al., "Low-Dose Sublingual Zolpidem Tartrate is Associated with Dose-Related Improvement in Sleep Onset and Duration in Insomnia Characterized by Middle-of-the-Night (MOTN) Awakenings," Sleep, 31(9):1277-1284(2008).

Scharf, M.B. "Individualizing therapy for early, middle-of-the-night and late-night insomnia." UCP Supplement 116: 20-24 (Jan. 2001).

Shangold, G. et al. "NovaDel NDA for Nitroglycerin Lingual Spray Is Accepted For Review by FDA." Khandaker Analytical Review 3(5): 28-30 (2004).

Singh et al., "Transmucosal Zolpidem: Pharmacokinetic and Pharmacodynamic Profile Supports Possible Middle-of-the-Night Dosing." American Psychiatric Association Meeting Abstract; May 20-25, 2006; Toronto Canada.

Squier, C. et al., "Lipid Content and Water Permeability of Skin and Oral Mucosa." The Journal of Investigative Dermatology 96(1):123-126 (1991).

Squier, C. et al., "Structure and Function of the Oral Mucosa and Implications for Drug Delivery." Oral Mucosa Drug Deliver. Ed. Michael J. Rathbone, New York: Marcel Dekker 1-26 (1996).

Tabak, L. et al., "Role of salivary mucins in the protection of the oral cavity." Journal of Oral Pathology 11: 1-17 (1982).

Thapa, P. et al., "Lyophilization of Unit Dose Pharmaceutical Dosage Forms." Drug Development and Industrial Pharmacy vol. 29, No. 5: 595-602 (2003).

Werth, E. et al., "Dynamics of the Sleep EEG after an early evening nap: experimental data and simulations." American Physiological Society R501-510 (1996).

Wertz, P.W. et al., "Cellular and Molecular Basis of Barrier Function in Oral Epithelium." Critical Reviews in Therapeutic Drug Carrier Systems 8(3): 237-269 (1991).

Zhang et al. "Oral Mucosal Drug Delivery—Clinical Pharmacokinetics and Therapeutic Applications." Drug Delivery Systems 41(9): 661-80 (2002).

U.S. Appl. No. 11/439,873, Singh et al.

U.S. Appl. No. 11/439,884, Singh et al.

U.S. Appl. No. 11/440,410, Singh et al.

Danjou et al., "A comparison of the residual effects of zaleplon and zolpidem following administration 5 to 2 h before awakening." Br. J. Clin. Pharmacol., 48:367-374 (1999).

Doghramji, "The need for flexibility in dosing of hypnotic agents." Sleep, 23 Suppl. 1:S16-20 (2000).

Greenblatt et al., "Comparative kinetics and dynamics of zaleplon, zolpidem, and placebo." Clin. Pharmacol. Therap., 64:553-561 (1998).

Greenblatt et al., "Kinetic and dynamic interaction study of zolpidem with ketoconazole, itraconazole, and fluconazole." Clin. Pharmacol. Therap., 64:661-671 (1998).

Hindmarch et al., "Residual effects of zaleplon and zolpidem following middle of the night administration five hours to one hour before awakening." Hum. Psychopharmacol., 16:159-167 (2001).

Lader, "Implications of hypnotic flexibility on patterns of clinical use." Int. J. Clin. Pract. Suppl., 116:14-19 (2001).

Merlotti et al., "The dose effects of zolpidem on the sleep of healthy normals." J. Clin. Psychopharmacol., 9:9-14 (1989).

Roth et al., "Transmucosal zolpidem (TMZ): pharmacokinetic (PK) and pharmacodynamic (PD) profile supports possible middle-of-the-night dosing." Amer. Psych. Assoc. Meeting Abstract; May 20-25, 2006; Toronto, Canada.

Khandakar Analytical Review, "NovaDel NDA for Nitroglycerin Lingual Spray is Accepted for Review by FDA", vol. 3, Issue 5, Aug. 2004, pp. 27-30.

Ambien® Package Insert, Sanfoi-Aventis, Bridgewater, NJ (Jun. 2008).

Borbely, A. et al., "Sleep Homeostasis and Models of Sleep Regulation." Principles and Practice of Sleep Medicine. Ed, Kryger, Roth and Dement. Saunders 3$^{rd}$ edition. 377-390 (2000).

Borbely, A., "A Two Process Model of Sleep Regulation." Human Neurobiology. 1:195-204 (1982).

Cziesler, C. et al., "The Human Circadian Timing System and Sleep Wake Regulation." Principles and Practice of Sleep Medicine. Ed. Kryger, Roth and Dement. Saunders 3$^{rd}$ edition. 353-375 (2000).

Hajak, G. et al., "'As needed' pharmacotherapy combined with stimulus control treatment in chronic insomnia—assessment of a novel intervention strategy in a primary care setting." Annals of Clinical Psychiatry. vol. 14, No, 1. 1-7 (Mar. 2002).

Hermann, W. et al., "Pilot Controlled Double-blind Study of Hypnotic Effects of Zolpidem in Patients with Chronic 'Learned' Insomnia: Psychometric and Polysomnographic Evaluation," J. Intl. Med. Research. vol. 21, 306-322 (1993).

Kudo, Y., "A dose finding study of zolpidem in chronic insomnia patients in multi-center cooperation." Clinical Pharmacology. vol. 15, Supplement 1, Part B. 76B (1992).

Priest, R. et al., "Efficacy of zolpidem in insomnia." European Psychiatry. vol. 12, Suppl. 1. 5S-14S (1997).

Richardson, G., "The Human Circadian System in Normal and Disordered Sleep." Journal of Clinical Psychiatry. 66 (Suppl 9). 3-9 (2005).

Roth, T. et al., As-needed Treatment of Insomnia Following MOTN Awakening: Clinical Efficacy of Low-Dose Zolpidem Tartrate Sublingual Lozenge. Sleep. vol. 32, A282, Abstract 0864 (2009).

Scharf, M. et al., "Safety and Efficacy of Long-Term Zolpidem Treatment in Insomniacs." Sleep Research, p. 87 (1990).

Shah, N. H. et al. "Evaluation of two new tablet lubricants—sodium stearyl fumarate and glyceryl behenate." Drug Development and Industrial Pharmacy. 12(8&9): 1329-1346 (1986).

Teitelbaum, J., "From Fatigued Fantastic! A proven program to regain vibrant health, based on a new scientific study showing effective treatment for chronic fatigue and fibromyalgia." New York: Avery. 112-119 (2001).

Verster, J. et al. "Residual Effects of Middle-of-the-Night Administration of Zaleplon and Zolpidem on Driving Ability, Memory Functions, and Psychomotor Performance." J. Clinical Psychopharmacology 22(6): 576-583 (2002).

Zammit, G. "Zalepion vs. Zolpidem: Differences in Next-Day Residual Sedation After Middle-of-the-Night Administration." 214 J. Sleep Res. vol. 9, Suppl. 1, Abstract 427 (2000).

AMBIEN® Prescribing Information. Physician's Desk Reference 2710-14 (1998).

Berge et al., "Pharmaceutical Salts." Journal of Pharmaceutical Sciences 66(1):1-19 (Jan. 1977).

Borbely et al., "Sleep Initiation and Initial Sleep Intensity: Interactions of Homeostatic and Circadian Mechanism." Journal of Biological Rhythms 4: 37-39 (1989).

Kosherek et al., "Dose effects of zolpidem in transient insomnia." Sleep Research 17:47 (1998).

Lahmeyer et al., "Subjective Efficacy of Zolpidern in Outpatients with Chronic Insomnia, A Double-Blind Comparison with Placebo." Clinical Drug Invest 13(3): 134-144 (1997).

Monti, "Effect of Zolpidem on Sleep in Insomniac Patients." European Journal of Clinical Pharmacology 36:461-466 (1989).

Declaration of Thomas Roth, Ph.D., filed in Inter Partes Reexamination of Alaux et al., USP 6,514,531 (extended Jun. 18, 2008).

Second Declaration of Thomas Roth, Ph,D., filed in Inter Partes Reexamination of Alaux et al., USP 6,514,531 (executed Oct. 28, 2009).

Roth et al., "Consensus for the Pharmacological Management of Insomnia in the New Millennium." IJCP 55(1): 42-52 (Jan./Feb. 2001).

Roth et al., "The Effects of Midazolam and Temazepan on Sleep and Performance when Administer in the Middle of the Night." 5(2): 66-69 (1985).

Roth et al., "Efficacy and safety of zolpidem-MR: A double-blind, placebo-controlled study in adults with primary insomnia." Sleep Medicine 7: 397-406 (2006).

Roth et al., "Zolpidem in the Treatment of Transient Insomnia: A Double-Blind, Randomized Comparison with Placebo." Sleep 18(4):246-251 (1995).

Roth et al., "Zolpidem—place in therapy," European Psychiatry 215-230 (1996).

Salva, P., and Costa, J., "Clinical Pharmacokinetics and Pharmacodynamic of Zolpidem." Clinical Pharmacokinetics 29(3):142-153 (1995).

Scharf et al., "Dose Response Effects of Zolpidem in Normal Geriatric Subjects." Journal of Clinical Psychiatry 52(2): 77-83 (Feb. 1991).

Scharf et al., "A Multicenter, Placebo-Controlled Study Evaluating Zolpidem in the Treatment of Chronic Insomnia." Journal of Clinical Psychiatry 55(5): 192-199 (May 1994).

Verbeeck et al., "Generic substitution: the use of medicinal products containing different salts and implications for safety and efficacy." European Journal of Pharmacological Sciences 28:1-6 (2006).

Walsh et al., "Eight Weeks of Non-Nightly Use of Zolpidem for Primary Insomnia." Sleep 23(8): 1-10 (2000).

Walsh et al., "Transient Insomnia Associate with a 3-Hour Phase Advance of Sleep Time and Treatment with Zolpidem," Journal of Clinical Psychopharmacology 10(3)184-189 (1990).

Walsh et al., Polysomnographic Studies of the Effects of Zolpidem in Patients with Insomnia in Zolpidem: An Update of its Pharmacological Properties and Therapeutic Place in the Management of Insomnia, Freeman et al., eds., Elsevier, publ. 1996, 137:128-139 (1996).

Greenblatt et al., "Dynamics and Kinetics of a Modified-Release Formulation of Zolpidem: Comparison with Immediate-Release Standard Zolpidem and Placebo," The Journal of Clinical Pharmacology 46: pp. 1469-1480 (2006) www.jclinpharm.org/cgi/content/adbstract/46/12/1469.

Mitler, M.M. "Nonselective and Selective Benzodiazepine Receptor Agonists—Where Are We Today?" Sleep vol. 23 (Supplement 1): S39-S47 (2000).

Walsh, J.K. et al. "Lack of Residual Sedation Following Middle-of-the-Night Zaleplon Administration in Sleep Maintenance Insomnia." Clinical Neuropharmacology vol. 3, No. 1: 17-21 (2000).

Zammit et al., "Sleep and Residual Sedation After Administration of Zalepon, Zolpidem, and Placebo during Experimental Middle-of-the-Night Awakening." Journal of Clinical Sleep Medicine vol. 2, No. 4: pp. 417-423 (2006).

U.S. Appl. No. 12/813,429, Singh.

U.S. Appl. No. 13/078,731, Singh.

"Treatment of Middle of the Night Insomnia: Current Therapeutic Approaches." 10th International Forum on Mood and Anxiety Disorders (IFMAD); Nov. 17-19, 2010; Vienna, Austria.

"The Nature and Prevalence of Middle-of-the-Night Hypnotic Use," Society of Biological Psychiatry 66th Annual Meeting; May 12-14, 2011; San Francisco, California.

* cited by examiner

METHODS OF TREATING MIDDLE-OF-THE-NIGHT INSOMNIA

CROSS-REFERENCES TO RELATED APPLICATIONS

This application claims priority to U.S. Provisional Application No. 60/684,842, filed May 25, 2005, U.S. Provisional Application No. 60/741,673, filed Dec. 1, 2005, U.S. Provisional Application No. 60/788,340, filed Mar. 31, 2006, and U.S. Provisional Application No. 60/788,249, filed Mar. 31, 2006, the disclosures of which are hereby incorporated by reference in their entirety for all purposes.

BACKGROUND OF THE INVENTION

Until recently, medical literature has recognized four types of insomnia, including sleep onset insomnia (e.g., trouble falling asleep at bedtime), sleep maintenance insomnia (e.g., disturbed sleep during the night), early morning awakening, and transient insomnia (e.g., new environment, first night in hotel syndrome). However, according to the National Sleep Foundation's 2005 "Sleep in America" poll, about 20% of total respondents and about 50% of respondents reporting insomnia symptoms complained of waking up too early and having difficulty returning to sleep at least a few nights a week (results available on the worldwide web at sleepfoundation.org). This type of insomnia includes "middle-of-the-night" insomnia, "late night" insomnia, "prolonged awakening after sleep onset" insomnia, "sleep maintenance" insomnia, and insomnia that follows after "middle-of-the-night" awakening, each of which has a component of interrupted sleep.

More particularly, patients with "middle-of-the-night" (MOTN) insomnia generally do not have problems initially falling asleep, but wake up prior to their intended wake time (during their normal sleep time), usually with about 3 to 4 hours of sleep time remaining. These patients require a treatment intervention that would reduce their wake time during their sleep time after awakening without leaving residual sedative effects in the morning. Unfortunately, currently available hypnotic medications are unsuitable for treating MOTN insomnia because they are slow to induce sleep (e.g., zaleplon) and/or require administration prior to about 7 to 9 hours in bed to avoid residual sleepiness in the morning (e.g., available dosage forms of zolpidem, eszopiclone, and zopiclone). Also, administration of most presently available hypnotics is prophylactic, resulting in unnecessary medication and overmedication of persons who require treatment for their MOTN insomnia a few nights a week.

Clearly, there remains a need for appropriate treatments for persons with MOTN insomnia. The present invention fulfills this and other needs.

BRIEF SUMMARY OF THE INVENTION

The present invention provides compositions and methods for treating MOTN insomnia with zolpidem or a salt thereof.

In one aspect, the present invention provides a solid unit dosage composition for the treatment of MOTN insomnia, the composition comprising an effective amount of zolpidem or a salt thereof, formulated for delivery of zolpidem across a subject's oral mucosa, wherein the effective amount is an amount of less than $1.30 \times 10^{-5}$ moles of zolpidem, and is an amount sufficient to produce a plasma concentration between about 25 ng/ml and about 50 ng/ml within 20 minutes of administration, when evaluated in an appropriate patient population.

In another aspect, the present invention provides a solid unit dosage composition for the treatment of MOTN insomnia, the composition comprising an amount of zolpidem or a salt thereof effective to produce sleep within 30 minutes of dosing a subject, but does not produce residual sedative effects when the subject is awakened at a time about 4 hours after dosing, when the composition is evaluated in an appropriate patient population.

In yet another aspect, the present invention provides a pharmaceutical composition suitable for absorption by the oral mucosa in the treatment of MOTN insomnia, the composition comprising from about 0.5 mg to about 4.0 mg of zolpidem or a salt thereof and a pharmaceutically acceptable excipient.

In a further aspect, the present invention provides a solid pharmaceutical composition for delivery across the oral mucosa for treating insomnia comprising zolpidem in an amount less than 5 mg and a buffer.

In a related aspect, the present invention provides a solid pharmaceutical composition for delivery across the oral mucosa for treating insomnia comprising zolpidem in an amount less than 5 mg and a binary buffer.

In another related aspect, the present invention provides a solid unit dosage pharmaceutical composition comprising a dose of zolpidem hemitartrate in an amount of less than 5 mg and a binary buffer system capable of raising the pH of a subject's saliva to a pH greater than about 8.5, irrespective of the starting pH of saliva, wherein the composition is formulated for delivery of zolpidem across the subject's oral mucosa.

In an additional aspect, the present invention provides a pharmaceutical composition for treating insomnia comprising zolpidem in an amount less than 5 mg and a binary buffer.

In a related aspect, the present invention provides a pharmaceutical composition for treating insomnia comprising zolpidem in an amount less than 5 mg and a binary buffer, wherein the composition is formulated for delivery of zolpidem across the oral mucosa and the binary buffer produces a saliva pH of at least 8.5, irrespective of the starting saliva pH.

In another aspect, the present invention provides a method of treating insomnia, the method comprising:
  administering to a subject who awakens from sleep and desires to return to sleep within 30 minutes and sleep for less than 5 hours, a single unit dosage composition comprising an effective amount of zolpidem or a salt thereof, formulated for delivery of zolpidem across the subject's oral mucosa,
  wherein the effective amount is an amount of less than $1.30 \times 10^{-5}$ moles of zolpidem, and is an amount sufficient to produce a plasma concentration between about 25 ng/ml and about 50 ng/ml within 20 minutes of administration, when evaluated in an appropriate patient population.

In a related aspect, the present invention provides a method of treating MOTN insomnia in a subject, the method comprising:
  administering to the subject a pharmaceutical composition comprising zolpidem or a salt thereof in an amount of less than $1.30 \times 10^{-5}$ moles of zolpidem,
  wherein the administering is on an as-needed basis, and wherein delivery of zolpidem occurs across the subject's oral mucosa to produce a blood level of zolpidem in the subject between about 25 ng/ml and about 50 ng/ml within about 20 minutes of administration and less than 20 ng/ml at a time 4 hours after administration.

In yet another aspect, the present invention provides a method of treating insomnia in a subject, the method comprising:

administering to the subject a pharmaceutical composition comprising zolpidem or a salt thereof, wherein the composition provides delivery of zolpidem across the subject's oral mucosa, wherein the subject is a subject who awakens from sleep and desires to resume sleep for less than 5 hours, and wherein the composition produces sleep within 30 minutes of dosing and the dose is such that it does not produce residual sedative effects when the subject is awakened at a time 4 hours after dosing.

In a further aspect, the present invention provides a method of treating insomnia in a subject, the method comprising:

administering a solid pharmaceutical composition comprising zolpidem in an amount less than 5 mg and a buffer, to a subject who awakens from sleep and desires to resume sleep for less than 5 hours, wherein the solid pharmaceutical composition provides delivery of zolpidem across the subject's oral mucosa, and wherein a blood level of zolpidem is achieved in the subject of between about 25 ng/ml and about 50 ng/ml within about 20 minutes of administration.

In a related aspect, the present invention provides a method of treating insomnia, the method comprising the steps of:

providing a solid pharmaceutical composition comprising zolpidem in an amount less than 5 mg and a buffer to a patient who awakens from sleep and desires to resume sleep for less than 5 hours; and administering the solid pharmaceutical composition to the patient for delivery of the zolpidem across the patient's oral mucosa, wherein a blood level of zolpidem in the patient is between about 25 ng/ml and about 50 ng/ml within about 20 minutes of administration.

In an additional aspect, the present invention provides a method of treating insomnia, the method comprising:

administering a solid pharmaceutical composition comprising zolpidem in an amount less than 5 mg and a binary buffer, to a subject who awakens from sleep and desires to resume sleep for less than 5 hours, wherein the solid pharmaceutical composition provides delivery of zolpidem across the subject's oral mucosa, wherein the solid pharmaceutical composition dissolves or disintegrates in about 2 minutes or less in the subject's mouth, and wherein the binary buffer raises the pH of saliva in the subject's mouth to a pH greater than about 9.0.

In a related aspect, the present invention provides a method of treating insomnia, the method comprising the steps of:

providing a solid pharmaceutical composition comprising zolpidem in an amount less than 5 mg and a binary buffer to a patient who awakens from sleep and desires to resume sleep for less than 5 hours; and administering the solid pharmaceutical composition to the patient for delivery of the zolpidem across the patient's oral mucosa, wherein the solid pharmaceutical composition dissolves or disintegrates in about 2 minutes or less in the patient's mouth, and wherein the binary buffer raises the pH of saliva in the patient's mouth to a pH greater than about 9.0.

Other objects, features, and advantages of the present invention will be apparent to one of skill in the art from the following detailed description and figures.

DETAILED DESCRIPTION OF THE INVENTION

I. General

Figure 1:
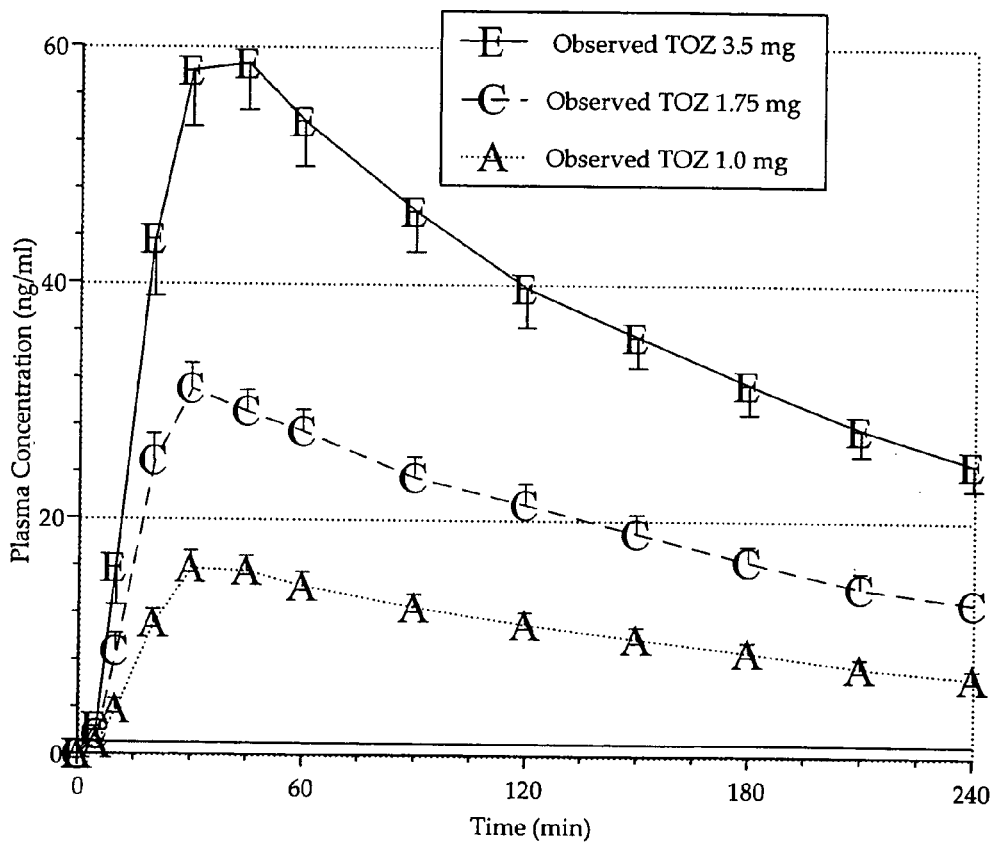
FIG. 1 shows the mean (SEM) plasma concentration time profiles of a 1.0 mg, 1.75 mg, and 3.5 mg sublingual zolpidem lozenge of the present invention.

The present invention provides compositions and methods for treating insomnia, particularly MOTN insomnia, using therapeutically effective low doses of zolpidem or a salt thereof by delivering zolpidem across the oral mucosa. The present invention is based, in part, upon the surprising discovery that low doses of zolpidem, when formulated for delivery across the oral mucosa, can induce rapid onset of sleep without residual sedative effects upon awakening 2-4 hours later. Advantages of taking a low dose amount of zolpidem (e.g., less than 5 mg or $1.30 \times 10^{-5}$ moles) to counteract MOTN insomnia include rapid action to induce sleep, treatment on an as-needed basis to avoid excessive and unnecessary medication, and no or minimal residual sedative effects upon awakening.

While there are various types of dosage forms, solid dosage forms for oral administration are perhaps among the most preferred by patients, and among the most prevalently used. Many of the dosage forms are medicaments formulated as tablets or capsules, which are swallowed. However, swallowed formulations have several disadvantages, including drug losses during hepatic first pass metabolism, during enzymatic degradation within the gastrointestinal tract, and during absorption to non-targeted tissues. These drug losses not only increase the variability in drug response, but also often require that the medicament be given in greater initial doses. Still further, as the drug has to pass through the gastrointestinal system in order to enter the blood stream, the time to reach a therapeutic effect may be quite long, typically around forty-five minutes or longer.

Drug delivery via the mucous membranes of the oral cavity has certain advantages, due to the properties of the oral mucosa itself. For example, the mucous membranes of the oral cavity are highly vascularized and well supplied with lymphatic drainage sites. In general, the mucous membranes of the oral cavity can be divided into five main regions: the floor of the mouth (sublingual), the cheeks (buccal), the gums (gingival), the roof of the mouth (palatal), and the lining of the lips. These regions differ from each other with respect to their anatomy, drug permeability, and physiological response to drugs. For example, in terms of permeability, sublingual is more permeable than buccal, which is more permeable than palatal. This permeability is generally based on the relative thickness and degree of keratinization of these membranes, with the sublingual mucosa being relatively thin and non-keratinized, the buccal mucosa being thicker and non-keratinized, and the palatal mucosa being intermediate in thickness, but keratinized.

Accordingly, in certain aspects, the present invention provides solid dosage forms containing low doses of zolpidem (e.g., dissolving tablets, lozenges, etc.) and methods for treating MOTN insomnia by administering such compositions to the oral mucosa to deliver and facilitate absorption of a substantial portion of the dose through the tissues of the buccal and/or sublingual cavity. In some embodiments, the solid dosage forms described herein facilitate buccal and/or sublingual absorption due to the presence of a buffer system (e.g., a bicarbonate/carbonate buffer system). Without being bound to any particular theory, the buffer system can promote the in situ conversion of a hydrophilic (i.e., charged) form of zolpidem (e.g., zolpidem hemitartrate) into its lipophilic free-base (i.e., neutral) form, which penetrates the lipid membranes in the oral mucosa more readily than the salt form. As a result, both non-elderly and elderly patients can benefit from taking a substantially lower dose of zolpidem (e.g., about 3.5 mg for non-elderly; about 1.75 mg for elderly) as compared to the lowest currently approved dose of 5 mg, thereby rapidly inducing sleep without residual sedative effects upon awakening.

It is also desirable to reduce variability in drug delivery. Surprisingly, this can be achieved by utilizing a binary buffer system capable of achieving and sustaining a final pH in the oral cavity, independent of the initial pH. Accordingly, compositions for delivering zolpidem or a salt thereof across the oral mucosa having a buffer system that produces a final pH, independent of the initial pH, and which sustains that final pH for a given period of time, are particularly desirable, and are provided herein.

II. Definitions

As used herein, the following terms have the meanings ascribed to them unless specified otherwise.

The term "sleep disorder" refers to a disruptive pattern of sleep arising from many causes including, without limitation, dysfunctional sleep mechanisms, abnormalities in physiological functions during sleep, abnormalities of the biological clock, and sleep disturbances that are induced by factors extrinsic to the sleep process. In particular, the term encompasses disorders associated with difficulties in staying asleep and/or falling asleep such as insomnia (e.g., transient, short-term, and chronic), delayed sleep phase syndrome, hypnotic-dependent sleep disorder, and stimulant-dependent sleep disorder; disorders associated with difficulties in staying awake such as sleep apnea, narcolepsy, restless leg syndrome, obstructive sleep apnea, central sleep apnea, idiopathic hypersomnia, respiratory muscle weakness-associated sleep disorder; disorders associated with difficulties in adhering to a regular sleep schedule such as sleep state misperception, shift work sleep disorder, chronic time zone change syndrome, and irregular sleep-wake syndrome; disorders associated with abnormal behaviors such as sleep terror disorder (i.e., parasomnia) and sleepwalking (i.e., somnambulism); and other disorders such as sleep bruxism, fibromyalgia, and nightmares.

The term "insomnia" refers to a sleep disorder characterized by symptoms including, without limitation, difficulty in falling asleep, difficulty in staying asleep, intermittent wakefulness, and/or waking up too early. The term also encompasses daytime symptoms such as sleepiness, anxiety, impaired concentration, impaired memory, and irritability. Types of insomnia suitable for treatment with the compositions of the present invention include, without limitation, transient, short-term, and chronic insomnia. The term "transient insomnia" refers to insomnia lasting for a few nights. The term "short-term insomnia" refers to insomnia lasting for about two to about four weeks. The term "chronic insomnia" refers to insomnia lasting for at least one month.

The phrase "prolonged awakening after sleep onset insomnia" refers to the condition wherein a subject, after falling asleep, awakens and has difficulty returning to sleep, regardless of the number of hours of time in bed remaining. "Prolonged awakening after sleep onset insomnia" includes middle-of-the-night insomnia, late night insomnia, and insomnia after early night awakening.

As used herein, the term "middle-of-the-night insomnia" or "MOTN insomnia" refers to the condition wherein a subject, after falling asleep, awakens and has difficulty returning to sleep. Typically, the subject has about 5 hours of sleep time or time in bed remaining, although in some subjects only 4 hours, 3 hours, or 2 hours of sleep time may remain. One of skill in the art will appreciate that the term middle-of-the-night refers to a middle portion of the subject's sleep time in any sleep period, rather than a specific time of a time zone, day or night. For example, a shift worker who would normally sleep from 8 am until 3 pm or 4 pm can still exhibit MOTN insomnia, when their sleep time is interrupted during normal daylight hours. MOTN insomnia can be transient, short-term, or chronic.

The term "time in bed" refers to the amount of time a subject spends in a recumbent position (e.g., lying down in bed or reclining in a chair) intending to sleep.

The term "sleep time" refers to the time that a subject spends sleeping. Sleep time can be continuous or discontinuous.

"Sleep efficiency" refers to the total sleep time a subject receives during their time in bed. Sleep efficiency is measured by the following equation:

$$100*(\text{total sleep time (TST)}/\text{total time in bed}).$$

The phrase "residual sedative effects" refers to a patient's subjective feeling of sedation upon awakening. Additionally, the term is meant to refer to a patient population as found in, for example, a clinical trial, rather than a single patient example. Residual sedative effects also can be evaluated using one or more of any of a number of tests exploring psychomotor performance, attention, information processing, and memory used by those of skill in the art including, for example, a Sleep Latency Test (SLT), a Visual Analog Test (VAT), a Digit Symbol Substitution Test (DSST), a Symbol Copying Test (SCT), a Critical Flicker Fusion threshold test (CFF), a Simple Reaction time test (visual or auditory; SRT), a Choice Reaction Time test (CRT), a Word Learning Test (WLT), a Critical Tracking Test (CTT), a Divided Attention Test (DAT), a digit or letter cancellation test, sleep staging through polysomnographic (PSG) measurements, Continuous Performance Task test (CPT), Multiple Sleep Latency Test (MSLT), a Rapid Visual Information Processing test (RVIP), a mental calculation test, a body sway test, a driving performance test, and others. Guidelines for a Sleep Latency Test are published in *Sleep* (1986) 9:519-24. The above-listed tests are described, for example, in Walsh, et al., (2000) *Clin Neuropharm* 23:17-21; Verster, et al., (2002) *J Clin Psychopharm* 22:576-583; Patat, et al, (2001) *Human Psychopharm* 16:369-392; and Hindmarch, et al., (2001) *Human Pshychopharm* 16:159-167. As a result, an amount that substantially avoids or does not produce residual sedative effects is an amount that allows a subject, upon awakening following sleep time, to test acceptably in at least one of the above tests, preferably at least two or three of the above tests, and most preferably in at least four of the above tests.

Alternatively, an amount that substantially avoids or does not produce residual sedative effects can be objectively measured by determining the plasma or serum levels of zolpidem at an appropriate time point. In particular, residual sedative effects will be essentially extinguished when a subject's plasma levels of zolpidem fall below about 20 ng/ml. Again, this objective test refers to an average zolpidem plasma or serum concentration in a patient population. Because some variability between patients is expected, a number of patients may respond as having residual sedative effects even at low plasma or serum concentrations of zolpidem.

The term "therapeutically effective amount" or "effective amount" refers to the amount of zolpidem that is capable of achieving a therapeutic effect in a subject in need thereof. For example, an effective amount of zolpidem can be the amount that is capable of preventing or relieving one or more symptoms associated with MOTN insomnia. It is important to note that a plasma concentration time curve for any given drug is illustrative of four, very often overlapping, kinetic events that decide the fate of the drug inside the body after the drug is administered. The four events are absorption, distribution, metabolism, and excretion. The absorption phase dominates in the beginning, while the distribution phase dominates at peak concentration time, and metabolism and excretion phases dominate the remaining disappearing stages of the drug. The sedative-hypnotic activity profile of zolpidem can be predicted from its plasma concentration time curve (Greenblatt et al., *Clin. Pharmacol. Therap.* 64:553 (1998)). In general, plasma concentrations between about 25 ng/ml and about 50 ng/ml, which are sufficient for inducing sleep, occur during the absorption phase of the drug, but this is not necessarily the peak concentration. Once the zolpidem is absorbed and distributed, the plasma concentrations will fall off with time. When the latter phase of drug distribution, metabolism, and excretion results in concentrations of zolpidem below about 20 ng/ml, the residual sedative effects of the drug will be essentially extinguished. This level will depend, to some extent, on the patient's age, hepatic efficiency, and initial dose. Generally, for the compositions and methods described herein, the sedative-hypnotic activity does not persist once the plasma levels have dropped below about 20 ng/ml, due to concurrence of continuous depletion of drug in the body and fulfillment of sleep requirement of the sleep-wake cycle of the body.

The term "bioavailability" refers to the rate and/or extent to which a drug is absorbed or becomes available to the treatment site in the body. The MOTN efficacy of zolpidem can also be improved by improving the bioavailability or the absorption of zolpidem, e.g., at rate of about 0.1 ng/ml per minute.

The term "dissolves" or "dissolution" refers to the conversion of a portion of the solid dosage form to a solution or slurry form. The amount of the solid dosage form that dissolves over a period of time will vary depending on the components of the dosage form (e.g., the form of zolpidem used as well as the excipients used). Some solid dosage forms will completely dissolve in a patient's mouth over a time period of about 15 minutes or less. Still other solid dosage forms will completely dissolve in the mouth over a time period of about 6 minutes or less. Generally, at least about 25% by weight of the solid dosage form will dissolve within about 5 minutes of administration. Suitable methods known in the art for determining the dissolution profile of a solid dosage form include, e.g., United States Pharmacopeia (USP) dissolution tests such as USP <711> Apparatus 1 or USP <711> Apparatus 2.

The term "disintegrates" or "disintegration" refers to the breakdown of, for example, a tablet or lozenge, into small pieces accompanied by complete dissolution of a substantial portion of the solid dosage form to a liquid form. More particularly, disintegration of a solid dosage form refers to less than about 25% by weight of the solid dosage form remaining in the mouth following an appropriate time period, e.g., about 5 minutes after administration. Suitable methods known in the art for determining the disintegration profile of a solid dosage form include, e.g., the USP disintegration test.

As used herein, the phrase "substantially complete conversion of zolpidem from its ionized to its un-ionized form" refers to greater than about 50% conversion of zolpidem from its ionized form into its un-ionized form. For example, a buffer system may favor at least about 50%, 55%, 60%, 65%, 70%, 75%, 80%, 85%, 90%, 95%, or 99% conversion of zolpidem from its ionized form into its un-ionized form. In some embodiments, the conversion occurs within about 10 minutes following administration.

The term "variability" refers to inter-subject variability in terms of the percent of relative standard deviation (RSD) for the maximum plasma concentration ($C_{max}$) and the time to reach the maximum plasma concentration ($T_{max}$). Notably, the preferred compositions of the present invention have an RSD for $C_{max}$ of about 33% versus about 45% for commercial oral tablets such as Ambien® tablets. Further, the compositions of the present invention have an RSD for $T_{max}$ of about 50% or less versus about 100% for commercial oral tablets such as Ambien® tablets.

The term "subject" or "patient" refers to humans.

The term "administering" refers to administration of the compositions of the present invention to the mucous membranes of the oral cavity (i.e., oral mucosa). Examples of suitable sites of administration within the oral mucosa include, without limitation, the mucous membranes of the floor of the mouth (sublingual mucosa), the cheeks (buccal mucosa), the gums (gingival mucosa), the roof of the mouth (palatal mucosa), the lining of the lips, and combinations thereof. Preferably, the compositions of the present invention are administered to the sublingual mucosa, buccal mucosa, or a combination thereof.

III. Description of the Embodiments

In one aspect, the present invention provides a solid unit dosage composition for the treatment of MOTN insomnia, the composition comprising an effective amount of zolpidem or a salt thereof, formulated for delivery of zolpidem across a subject's oral mucosa, wherein the effective amount is an amount of less than $1.30 \times 10^{-5}$ moles of zolpidem, and is an amount sufficient to produce a plasma concentration between about 25 ng/ml and about 50 ng/ml within 20 minutes of administration, when evaluated in an appropriate patient population.

In one embodiment, the solid unit dosage composition provides about 50% of the maximum plasma concentration ($C_{max}$) of zolpidem in about 30 minutes or less, alternatively in about 20 minutes or less, or alternatively in about 10 minutes or less. In another embodiment, the solid unit dosage composition provides blood (e.g., plasma) levels of zolpidem that are less than about 20 ng/ml at a time about 2, 3, or 4 hours after dosing. The zolpidem is typically delivered across the subject's sublingual and/or buccal mucosa.

In some embodiments, the solid unit dosage composition comprises at least one pH-adjusting agent selected from the group consisting of a carbonate salt and a bicarbonate salt. In other embodiments, the solid unit dosage composition comprises a binary buffer system that raises the pH of the subject's saliva to a pH greater than about 8.5, alternatively greater than about 9.0, alternatively greater than about 9.5, alternatively greater than about 10.0, alternatively greater than about 10.5, alternatively greater than about 11.0, or alternatively between about 9.0 and about 11.0, irrespective of the starting pH of saliva. For example, the binary buffer system can comprise sodium carbonate and sodium bicarbonate. Alternatively, the binary buffer system can comprise any combination of carbonate salt and bicarbonate salt known in the art.

The solid unit dosage composition is typically in the form of a lozenge, a chewing gum, a chewable tablet, or a dissolving tablet such as a slow-dissolving tablet or a quick-dissolving tablet. Preferably, the solid unit dosage composition is a lozenge or a quick-dissolving tablet. A quick-dissolving tablet usually provides complete dissolution in the subject's mouth in less than about 0.5 minutes, alternatively in less than about 1 minute, alternatively in less than about 1.5 minutes, alternatively in less than about 2 minutes, alternatively in less than about 2.5 minutes, alternatively in less than about 3 minutes, alternatively in less than about 4 minutes, alternatively in less than about 5 minutes, or alternatively in less than about 6 minutes. A description of low dose zolpidem lozenge and tablet dosage forms is provided in Examples 1 and 3, respectively.

In another embodiment, the solid unit dosage composition contains less than about 5 mg of zolpidem hemitartrate. Preferably, the solid unit dosage composition contains from about 0.5 to about 4.75 mg of zolpidem hemitartrate, alternatively from about 1.5 to about 2.5 mg of zolpidem hemitartrate, or alternatively from about 3.0 to about 3.75 mg of zolpidem hemitartrate.

The effective amount of zolpidem is generally evaluated in an appropriate patient population (e.g., a patient population used for a clinical study) based on factors such as age, weight, the number of hours of time in bed remaining, and/or the ability of a subject to metabolize zolpidem. Accordingly, effective amounts of zolpidem for delivery across the oral mucosa may be different for selected patient populations. For example, the effective amount of zolpidem in an elderly patient population (i.e., subjects 65 years of age and older) is usually from about 1.5 mg to about 2.5 mg of zolpidem, alternatively about 1.75 mg, alternatively about 2.0 mg, or alternatively about 2.5 mg. Similarly, the effective amount of zolpidem in a population of subjects with a diminished capacity to metabolize zolpidem can be from about 1.5 mg to about 2.5 mg of zolpidem, alternatively about 1.75 mg, alternatively about 2.0 mg, or alternatively about 2.5 mg. The effective amount of zolpidem in a non-elderly patient population (i.e., subjects younger than 65 years of age) is usually from about 3.0 mg to about 3.75 mg zolpidem, alternatively about 3.25 mg, alternatively about 3.5 mg, or alternatively about 3.75 mg. The effective amount of zolpidem in subjects who have awakened but still have about 4 or 5 hours of time in bed remaining can be from about 2 mg to about 5 mg of zolpidem. A lower amount of zolpidem (e.g., from about 0.5 mg to about 2.5 mg, alternatively about 0.5 mg, alternatively about 1.0 mg, alternatively about 1.5 mg, alternatively about 2.0 mg, or alternatively about 2.5 mg) can be administered to subjects who have awakened but still have about 2 to 4 hours of time in bed remaining.

Any method known in the art can be used to determine the plasma concentration of zolpidem in a subject. As a non-limiting example, the plasma from a blood sample collected from the subject can be assayed for zolpidem levels using high pressure liquid chromatography (HPLC) followed by tandem mass spectrometry (MS) or fluorescence detection. Chromatographic methods for measuring plasma levels of zolpidem are described in, for example, Ascalone et al., *J. Chromatogr.*, 581:237-250 (1992); Tracqui et al., *J. Chromatogr.*, 616:95-103 (1993); Durol et al., *J. Anal. Toxicol.*, 215:388-392 (1997); Ptacek et al., *J. Chromatogr. B Biomed. Sci. Appl.*, 694:409-413 (1997); and Ring et al., *J. Pharm. Biomed. Anal.*, 22:495-504 (2000).

In another aspect, the present invention provides a solid unit dosage composition for the treatment of MOTN insomnia, the composition comprising an amount of zolpidem or a salt thereof effective to produce sleep within 30 minutes of dosing a subject, but does not produce residual sedative effects when the subject is awakened at a time about 4 hours after dosing, when the composition is evaluated in an appropriate patient population.

In some embodiments, the solid unit dosage composition further comprises at least one pH-adjusting agent. Examples of pH-adjusting agents include, but are not limited to, carbonate salts, bicarbonate salts, and mixtures thereof. In other embodiments, the solid unit dosage composition comprises a binary buffer system. As a non-limiting example, the binary buffer system can comprise a carbonate salt (e.g., sodium carbonate) and a bicarbonate salt (e.g., sodium bicarbonate). In a preferred embodiment, the solid unit dosage composition is in a dosage form suitable for delivery of zolpidem across the subject's oral mucosa (e.g., buccal and/or sublingual delivery), wherein the binary buffer system raises the pH of the subject's saliva to a pH greater than about 8.5, alternatively greater than about 9.0, alternatively greater than about 9.5, alternatively greater than about 10.0, alternatively greater than about 10.5, alternatively greater than about 11.0, or alternatively between about 9.0 and about 11.0, irrespective of the starting pH of saliva.

In certain embodiments, the solid unit dosage composition produces polysomnography stage 1 sleep at the onset of sleep. Polysomnography stage 1 sleep typically refers to a non-REM stage of sleep where a polysomnogram shows about a 50% reduction in activity from wakefulness. The eyes are usually closed during polysomnography stage 1 sleep, but if aroused from it, a subject may feel as if he or she has not slept. Polysomnography stage 1 sleep may last for about 5 to about 10 minutes.

In another embodiment, the solid unit dosage composition contains less than about 5 mg of zolpidem hemitartrate. Preferably, the solid unit dosage composition contains from about 0.5 to about 4.75 mg of zolpidem hemitartrate, alternatively from about 1.5 to about 2.5 mg of zolpidem hemitartrate, or alternatively from about 3.0 to about 3.75 mg of zolpidem hemitartrate.

The solid unit dosage composition is typically in the form of a lozenge, a tablet (e.g., chewable tablet, slow-dissolving tablet, quick-dissolving tablet), or a chewing gum. Preferably, the composition is a lozenge or a quick-dissolving tablet. In some embodiments, the solid unit dosage composition provides buccal and/or sublingual dissolution in about 5 minutes or less (e.g., about 4, 3, 2, 1, or 0.5 minutes or less) following administration.

In yet another aspect, the present invention provides a pharmaceutical composition suitable for absorption by the oral mucosa (e.g., buccal and/or sublingual absorption) in the treatment of MOTN insomnia, the composition comprising from about 0.5 mg to about 4.0 mg of zolpidem or a salt thereof and a pharmaceutically acceptable excipient.

In some embodiments, the pharmaceutical composition comprises from about 0.5 to about 4.0 mg of zolpidem hemitartrate. Generally, the pharmaceutical composition can comprise about 1.0 mg, alternatively about 1.75 mg, alternatively about 2.5 mg, alternatively about 3.0 mg, or alternatively about 3.5 mg, of zolpidem or a salt thereof such as zolpidem hemitartrate. In other embodiments, the pharmaceutical composition further comprises a binary buffer system. For example, the binary buffer system can comprise a carbonate such as sodium carbonate and a bicarbonate such as sodium bicarbonate. The carbonate and bicarbonate are usually present in a carbonate:bicarbonate ratio of from about 1:1.0 to about 1:1.4 by weight, or alternatively from about 1:1.0 to about 1:1.2 by weight. Preferably, the binary buffer system raises the pH of the subject's saliva to a pH greater than about 8.5, alternatively greater than about 9.0, alternatively greater than about 9.5, alternatively greater than about 10.0, alternatively greater than about 10.5, alternatively greater than about 11.0, or alternatively between about 9.0 and about 11.0, irrespective of the starting pH of saliva.

In certain embodiments, the pharmaceutical composition is a solid unit dosage form such as a lozenge or tablet (e.g., chewable tablet, slow-dissolving tablet, quick-dissolving tablet). In another embodiment, the pharmaceutical composition provides complete buccal and/or sublingual dissolution in about 5 minutes or less (e.g., about 4, 3, 2, 1, or 0.5 minutes or less) following administration.

In a further aspect, the present invention provides a solid pharmaceutical composition for delivery across the oral mucosa for treating insomnia comprising zolpidem in an amount less than 5 mg and a buffer.

Generally, the buffer comprises a carbonate buffer, a bicarbonate buffer, or a mixture thereof. In certain instances, the buffer is a binary buffer comprising, e.g., a carbonate buffer and a bicarbonate buffer.

In some embodiments, the amount of zolpidem is less than about $1.30 \times 10^{-5}$ moles of zolpidem. In other embodiments, the amount of zolpidem is from about 0.5 to about 4.75 mg of zolpidem hemitartrate, e.g., from about 1.5 to about 2.5 mg of zolpidem hemitartrate, alternatively from about 3.0 to about 3.75 mg of zolpidem hemitartrate, alternatively from about 1.0 to about 3.75 mg of zolpidem hemitartrate, or alternatively from about 1.5 to about 3.0 mg of zolpidem hemitartrate.

The solid pharmaceutical composition is typically in a dosage form including, but not limited to, a lozenge, a chewing gum, a chewable tablet, and a dissolving tablet such as a slow-dissolving tablet or a quick-dissolving tablet. Preferably, the solid pharmaceutical composition is in the form of a lozenge or a quick-dissolving sublingual tablet. The zolpidem is typically delivered across the sublingual and/or buccal mucosa.

In a related aspect, the present invention provides a solid pharmaceutical composition for delivery across the oral mucosa for treating insomnia comprising zolpidem in an amount less than about 5 mg and a binary buffer.

In one embodiment, the amount of zolpidem is from about 0.5 to about 4.75 mg of zolpidem hemitartrate. Preferably, the amount of zolpidem is from about 1.5 to about 2.5 mg of zolpidem hemitartrate, alternatively from about 3.0 to about 3.75 mg of zolpidem hemitartrate, alternatively from about 1.0 to about 3.75 mg of zolpidem hemitartrate, or alternatively from about 1.5 to about 3.0 mg of zolpidem hemitartrate. In certain other instances, the amount of zolpidem is less than about $1.30 \times 10^{-5}$ moles of zolpidem.

In some embodiments, the binary buffer comprises a carbonate buffer such as sodium carbonate and a bicarbonate buffer such as sodium bicarbonate. Preferably, the solid pharmaceutical composition is a lozenge or tablet such as a sublingual tablet.

In another related aspect, the present invention provides a solid unit dosage pharmaceutical composition comprising a dose of zolpidem hemitartrate in an amount of less than about 5 mg and a binary buffer system capable of raising the pH of a subject's saliva to a pH greater than about 8.5, alternatively greater than about 9.0, alternatively greater than about 9.5, alternatively greater than about 10.0, alternatively greater than about 10.5, alternatively greater than about 11.0, or alternatively between about 9.0 and about 11.0, irrespective of the starting pH of saliva, wherein the composition is formulated for delivery of zolpidem across the subject's oral mucosa.

In one embodiment, the solid unit dosage pharmaceutical composition contains from about 0.5 to about 4.75 mg of zolpidem hemitartrate. Preferably, the solid unit dosage pharmaceutical composition contains from about 1.5 to about 2.5 mg of zolpidem hemitartrate, alternatively from about 3.0 to about 3.75 mg of zolpidem hemitartrate, alternatively from about 1.0 to about 3.75 mg of zolpidem hemitartrate, or alternatively from about 1.5 to about 3.0 mg of zolpidem hemitartrate.

In some embodiments, the binary buffer system comprises a carbonate salt such as sodium carbonate and a bicarbonate salt such as sodium bicarbonate. In other embodiments, the binary buffer system comprises a carbonate salt and a bicarbonate salt in a carbonate:bicarbonate ratio of from about 1:1.0 to about 1:1.4 by weight, or alternatively from about 1:1.0 to about 1:1.2 by weight.

In an additional aspect, the present invention provides a pharmaceutical composition for treating insomnia comprising zolpidem in an amount less than 5 mg and a binary buffer.

The pharmaceutical composition is typically in a dosage form suitable for delivery of zolpidem across a subject's oral mucosa (e.g., buccal and/or sublingual delivery) including, but not limited to, a lozenge, a chewing gum, a chewable tablet, and a dissolving tablet such as a slow-dissolving tablet or a quick-dissolving tablet. In some embodiments, the binary buffer comprises a carbonate buffer such as sodium carbonate and a bicarbonate buffer such as sodium bicarbonate. Alternatively, the binary buffer can comprise any combination of carbonate salt and bicarbonate salt known in the art.

In a related aspect, the present invention provides a pharmaceutical composition for treating insomnia comprising zolpidem in an amount less than 5 mg and a binary buffer, wherein the composition is formulated for delivery of zolpidem across the oral mucosa (e.g., buccal and/or sublingual mucosa) and the binary buffer produces a saliva pH of at least about 8.5, alternatively at least about 9.0, alternatively at least about 9.5, alternatively at least about 10.0, alternatively at least about 10.5, alternatively at least about 11.0, or alternatively between about 9.0 and about 11.0, irrespective of the starting saliva pH.

In another aspect, the present invention provides a method of treating insomnia, the method comprising:
  administering to a subject who awakens from sleep and desires to return to sleep within 30 minutes and sleep for less than 5 hours, a single unit dosage composition comprising an effective amount of zolpidem or a salt thereof, formulated for delivery of zolpidem across the subject's oral mucosa,
  wherein the effective amount is an amount of less than $1.30 \times 10^{-5}$ moles of zolpidem, and is an amount sufficient to produce a plasma concentration between about 25 ng/ml and about 50 ng/ml within 20 minutes of administration, when evaluated in an appropriate patient population.

In the methods of the present invention, the single unit dosage composition is typically administered pro re nata ("as needed"). Preferably, the single unit dosage composition is a lozenge or tablet (e.g., chewable tablet, slow-dissolving tablet, quick-dissolving tablet) formulated for buccal and/or sublingual delivery of zolpidem. In some embodiments, the single unit dosage composition further comprises a binary buffer system that raises the pH of the subject's saliva to a pH greater than about 8.5, alternatively greater than about 9.0, alternatively greater than about 9.5, alternatively greater than about 10.0, alternatively greater than about 10.5, alternatively greater than about 11.0, or alternatively between about 9.0 and about 11.0, irrespective of the starting pH of saliva.

In a preferred embodiment, the single unit dosage composition comprises from about 0.5 to about 4.75 mg of zolpidem hemitartrate and a binary buffer system that raises the pH of the subject's saliva to a pH greater than about 8.5, alternatively greater than about 9.0, alternatively greater than about 9.5, alternatively greater than about 10.0, alternatively greater than about 10.5, alternatively greater than about 11.0, or alternatively between about 9.0 and about 11.0, irrespective of the starting pH of saliva. In one embodiment, the binary buffer system comprises sodium carbonate and sodium bicarbonate.

In a related aspect, the present invention provides a method of treating MOTN insomnia in a subject, the method comprising:

administering to the subject a pharmaceutical composition comprising zolpidem or a salt thereof in an amount of less than $1.30 \times 10^{-5}$ moles of zolpidem, wherein the administering is on an as-needed basis, and wherein delivery of zolpidem occurs across the subject's oral mucosa to produce a blood level of zolpidem in the subject between about 25 ng/ml and about 50 ng/ml within about 20 minutes of administration and less than 20 ng/ml at a time 4 hours after administration.

In one embodiment, the pharmaceutical composition provides blood (e.g., plasma) levels of zolpidem in the subject between about 25 ng/ml and about 50 ng/ml within about 20, 30, or 40 minutes of administration and less than about 20 ng/ml at a time about 2, 3, or 4 hours after administration. In another embodiment, the pharmaceutical composition provides about 50% of the maximum plasma concentration ($C_{max}$) of zolpidem in about 30 minutes or less, alternatively in about 20 minutes or less, or alternatively in about 10 minutes or less, following administration. Methods for determining the blood (e.g., plasma) level of zolpidem in a subject are described above. The delivery of zolpidem typically occurs across the subject's sublingual and/or buccal mucosa.

In some embodiments, the pharmaceutical composition comprises at least one pH-adjusting agent. Examples of pH-adjusting agents include, but are not limited to, carbonate salts, bicarbonate salts, and mixtures thereof. In other embodiments, the pharmaceutical composition comprises a binary buffer system that raises the pH of the subject's saliva to a pH greater than about 8.5, alternatively greater than about 9.0, alternatively greater than about 9.5, alternatively greater than about 10.0, alternatively greater than about 10.5, alternatively greater than about 11.0, or alternatively between about 9.0 and about 11.0, irrespective of the starting pH of saliva. For example, the binary buffer system can comprise sodium carbonate and sodium bicarbonate. Alternatively, the binary buffer system can comprise any combination of carbonate salt and bicarbonate salt known in the art.

The pharmaceutical composition is typically in the form of a lozenge, a chewing gum, a chewable tablet, or a dissolving tablet such as a slow-dissolving tablet or a quick-dissolving tablet (e.g., quick-dissolving sublingual tablet). In another embodiment, the pharmaceutical composition contains less than about 5 mg of zolpidem hemitartrate. An effective amount of zolpidem to be administered on an as-needed basis according to the methods of the present invention is described above. Preferably, the pharmaceutical composition contains from about 0.5 to about 4.75 mg of zolpidem hemitartrate, alternatively from about 1.5 to about 2.5 mg of zolpidem hemitartrate, or alternatively from about 3.0 to about 3.75 mg of zolpidem hemitartrate. In certain instances, the pharmaceutical composition comprises less than a 5 mg dose of zolpidem hemitartrate and a binary buffer system consisting of a carbonate salt and a bicarbonate salt.

In yet another aspect, the present invention provides a method of treating insomnia in a subject, the method comprising:

administering to the subject a pharmaceutical composition comprising zolpidem or a salt thereof, wherein the composition provides delivery of zolpidem across the subject's oral mucosa, wherein the subject is a subject who awakens from sleep and desires to resume sleep for less than 5 hours, and wherein the composition produces sleep within 30 minutes of dosing and the dose is such that it does not produce residual sedative effects when the subject is awakened at a time 4 hours after dosing.

In one embodiment, the pharmaceutical composition produces sleep within about 20, 30, or 40 minutes of dosing but does not produce residual sedative effects when the subject is awakened at a time about 2, 3, or 4 hours after dosing. In certain instances, the pharmaceutical composition produces polysomnography stage 1 sleep at the onset of sleep.

In another embodiment, the pharmaceutical composition produces blood (e.g., plasma) levels of zolpidem in the subject between about 25 ng/ml and about 50 ng/ml within about 20, 30, or 40 minutes of administration and/or less than about 20 ng/ml at a time about 2, 3, or 4 hours after administration. In yet another embodiment, the pharmaceutical composition provides about 50% of the maximum plasma concentration ($C_{max}$) of zolpidem in about 30 minutes or less, alternatively in about 20 minutes or less, or alternatively in about 10 minutes or less, following administration. The zolpidem is typically delivered across the subject's sublingual and/or buccal mucosa.

In some embodiments, the pharmaceutical composition further comprises at least one pH-adjusting agent. In other embodiments, the pharmaceutical composition further comprises a binary buffer system that raises the pH of the subject's saliva to a pH greater than about 8.5, alternatively greater than about 9.0, alternatively greater than about 9.5, alternatively greater than about 10.0, alternatively greater than about 10.5, alternatively greater than about 11.0, or alternatively between about 9.0 and about 11.0, irrespective of the starting pH of saliva. Preferably, the pharmaceutical composition comprises zolpidem hemitartrate, e.g., in an amount of less than about 5 mg. In certain instances, the pharmaceutical composition comprises from about 0.5 to about 4.75 mg of zolpidem hemitartrate, e.g., from about 1.5 to about 2.5 mg of zolpidem hemitartrate, alternatively from about 3.0 to about 3.75 mg of zolpidem hemitartrate, alternatively from about 1.0 to about 3.75 mg of zolpidem hemitartrate, or alternatively from about 1.5 to about 3.0 mg of zolpidem hemitartrate.

In a preferred embodiment, the pharmaceutical composition comprises from about 1.5 to about 2.5 mg of zolpidem hemitartrate or from about 3.0 to about 3.75 mg of zolpidem hemitartrate and a binary buffer system consisting of sodium carbonate and sodium bicarbonate.

The pharmaceutical composition is typically in a solid unit dosage form including, but not limited to, a lozenge, a chewing gum, a chewable tablet, and a dissolving tablet such as a slow-dissolving tablet or a quick-dissolving tablet. Preferably, the pharmaceutical composition is in the form of a lozenge or a quick-dissolving sublingual tablet.

In a further aspect, the present invention provides a method of treating insomnia in a subject, the method comprising:
administering a solid pharmaceutical composition comprising zolpidem in an amount less than 5 mg and a buffer, to a subject who awakens from sleep and desires to resume sleep for less than 5 hours,
wherein the solid pharmaceutical composition provides delivery of zolpidem across the subject's oral mucosa, and wherein a blood level of zolpidem is achieved in the subject of between about 25 ng/ml and about 50 ng/ml within about 20 minutes of administration.

In a related aspect, the present invention provides a method of treating insomnia, the method comprising the steps of:
providing a solid pharmaceutical composition comprising zolpidem in an amount less than 5 mg and a buffer to a patient who awakens from sleep and desires to resume sleep for less than 5 hours; and
administering the solid pharmaceutical composition to the patient for delivery of the zolpidem across the patient's oral mucosa,
wherein a blood level of zolpidem in the patient is between about 25 ng/ml and about 50 ng/ml within about 20 minutes of administration.

In one embodiment, the solid pharmaceutical composition achieves a blood (e.g., plasma) level of zolpidem in the subject between about 25 ng/ml and about 50 ng/ml within about 20, 30, or 40 minutes of administration. In another embodiment, the solid pharmaceutical composition provides a blood level of zolpidem in the subject less than about 20 ng/ml within about 2, 3, or 4 hours of administration.

In some embodiments, the solid pharmaceutical composition dissolves or disintegrates in the subject's mouth in about 2 minutes or less (e.g., about 2, 1.5, 1, or 0.5 minutes or less). In other embodiments, the solid pharmaceutical composition dissolves or disintegrates in the subject's mouth in about 3 to about 6 minutes (e.g., about 3, 3.5, 4, 4.5, 5, 5.5, or 6 minutes). The zolpidem is typically delivered across the subject's sublingual and/or buccal mucosa.

Generally, the buffer that is present in the pharmaceutical composition raises the pH of saliva in the subject's mouth to a pH greater than about 8.5, alternatively greater than about 9.0, alternatively greater than about 9.5, alternatively greater than about 10.0, alternatively greater than about 10.5, alternatively greater than about 11.0, or alternatively between about 9.0 and about 11.0, irrespective of the starting pH of saliva. Preferably, the pH of the saliva is raised above about 9.0 for at least about 2 minutes (e.g., about 2, 2.5, 3, 3.5, 4, 4.5, 5, 5.5, 6, or more minutes). In certain instances, the buffer is a binary buffer. A non-limiting example of a suitable binary buffer includes a mixture of a carbonate buffer and a bicarbonate buffer.

In an additional aspect, the present invention provides a method of treating insomnia, the method comprising:
administering a solid pharmaceutical composition comprising zolpidem in an amount less than 5 mg and a binary buffer, to a subject who awakens from sleep and desires to resume sleep for less than 5 hours,
wherein the solid pharmaceutical composition provides delivery of zolpidem across the subject's oral mucosa, wherein the solid pharmaceutical composition dissolves or disintegrates in about 2 minutes or less in the subject's mouth, and wherein the binary buffer raises the pH of saliva in the subject's mouth to a pH greater than about 9.0.

In a related aspect, the present invention provides a method of treating insomnia, the method comprising the steps of:
providing a solid pharmaceutical composition comprising zolpidem in an amount less than 5 mg and a binary buffer to a patient who awakens from sleep and desires to resume sleep for less than 5 hours; and
administering the solid pharmaceutical composition to the patient for delivery of the zolpidem across the patient's oral mucosa,
wherein the solid pharmaceutical composition dissolves or disintegrates in about 2 minutes or less in the patient's mouth, and wherein the binary buffer raises the pH of saliva in the patient's mouth to a pH greater than about 9.0.

In one embodiment, the solid pharmaceutical composition achieves a blood (e.g., plasma) level of zolpidem in the subject between about 25 ng/ml and about 50 ng/ml within about 20, 30, or 40 minutes of administration. In another embodiment, the solid pharmaceutical composition provides a blood level of zolpidem in the subject less than about 20 ng/ml within about 2, 3, or 4 hours of administration.

In some embodiments, the pH of the saliva is raised above about 9.0 for at least about 2 minutes (e.g., 2, 2.5, 3, 3.5, 4, 4.5, 5, 5.5, 6, or more minutes). In other embodiments, the binary buffer comprises a carbonate buffer and a bicarbonate buffer. The zolpidem is typically delivered across the subject's sublingual and/or buccal mucosa.

IV. Compositions

Typically, the compositions of the present invention will contain zolpidem or a salt thereof in an amount of about 0.5 mg, about 0.8 mg, about 1.0 mg, about 1.5 mg, about 1.75 mg, about 2.0 mg, about 2.5 mg, about 3.0 mg, about 3.5 mg, about 3.75 mg, about 4.0 mg, about 4.5 mg, or about 4.75 mg per administration. However, the amount of zolpidem can be any dose amount less than about 5 mg, alternatively from about 1.5 to about 2.5 mg, or alternatively from about 3.0 to about 3.75 mg. One skilled in the art will appreciate that the amount of zolpidem can be expressed as the number of moles of zolpidem present in the composition. For example, 5 mg of zolpidem hemitartrate is equivalent to about $1.30 \times 10^{-5}$ moles of zolpidem. As such, in some embodiments, the composition will contain an amount of zolpidem hemitartrate that provides less than about $1.30 \times 10^{-5}$ moles of zolpidem.

Any form of zolpidem is suitable for use in the compositions described herein, e.g., a salt form of zolpidem, a free base form of zolpidem, a polymorph of zolpidem, or a mixture thereof. For example, pharmaceutically acceptable salts of zolpidem can include, without limitation, tartrate, hemitartrate, succinate, dihydrochloride, salicylate, hemisuccinate, citrate, maleate, hydrochloride, carbamate, sulfate, nitrate, and benzoate salt forms, as well as combinations thereof. In some embodiments, the zolpidem is in the form of a salt, e.g., zolpidem hemitartrate. In other embodiments, the zolpidem is in the form of a polymorph, e.g., commercially available from Plantex Ltd. (Netanya, Israel).

The compositions of the present invention may take the form of solid, semi-solid, lyophilized powder, or liquid dosage forms, such as, for example, tablets (e.g., chewable, slow-dissolving, quick-dissolving, etc.), pills, capsules, lozenges, gums, powders, solutions, suspensions, emulsions, aerosols, foams, creams, gels, lotions, or the like. Preferably, the compositions of the present invention are formulated as a tablet or a lozenge, in particular quick-dissolving tablets or lozenges, such as those described in U.S. Patent Publication No. 20050226925.

As used herein, the term "unit dosage" or "dosage form" refers to physically discrete units suitable as unitary dosages for human subjects and other mammals, each unit containing a predetermined quantity of therapeutic agent calculated to produce the desired onset, tolerability, and therapeutic effects, in association with one or more suitable pharmaceutical excipients such as carriers. Methods for preparing such dosage forms are known or will be apparent to those skilled in the art. For example, in some embodiments, a chewing gum dosage form of the present invention can be prepared according to the procedures set forth in U.S. Pat. No. 4,405,647. In other embodiments, a liquid spray or a solution, tincture, tablet, lozenge, or candy dosage form of the present invention can be prepared according to the procedures set forth, for example, in Remington: The Science and Practice of Pharmacy, 20$^{th}$ Ed., Lippincott, Williams & Wilkins (2003); Pharmaceutical Dosage Forms, Volume 1: Tablets, 2$^{nd}$ Ed., Marcel Dekker, Inc., New York, N.Y. (1989); and similar publications. The dosage form to be administered will, in any event, contain a quantity of the therapeutic agent in a therapeutically effective amount for relief of the condition being treated when administered in accordance with the teachings of the present invention.

The terms "carrier" or "excipient" refer to a typically inert substance used as a diluent or vehicle for a drug such as a therapeutic agent. The term also encompasses a typically inert substance that imparts cohesive qualities to the composition. Suitable carriers for use in the compositions of the present invention include, without limitation, a binder, a gum base, and combinations thereof. Non-limiting examples of binders include mannitol, sorbitol, xylitol, maltodextrin, lactose, dextrose, sucrose, glucose, inositol, powdered sugar, molasses, starch, cellulose, microcrystalline cellulose, polyvinylpyrrolidone, acacia gum, guar gum, tragacanth gum, alginate, extract of Irish moss, panwar gum, ghatti gum, mucilage of isapol husks, Veegum®, larch arabogalactan, gelatin, methylcellulose, ethylcellulose, carboxymethylcellulose, hydroxypropylmethylcellulose, polyoxyethylene polymers, polyacrylic acid (e.g., Carbopol), calcium silicate, calcium phosphate, dicalcium phosphate, calcium sulfate, kaolin, sodium chloride, polyethylene glycol, propylene glycol, and combinations thereof. These binders can be pre-processed to improve their flowability and taste by methods known in the art such as freeze drying (see, e.g., Fundamentals of Freeze-Drying, *Pharm. Biotechnol.*, 14:281-360 (2002); Lyophililization of Unit Dose Pharmaceutical Dosage Forms, *Drug. Dev. Ind. Pharm.*, 29:595-602 (2003)); solid-solution preparation (see, e.g., U.S. Pat. No. 6,264,987); and lubricant dusting and wet-granulation preparation with a suitable lubricating agent (see, e.g., *Remington: The Science and Practice of Pharmacy*, supra). For example, Mannogem® and Sorbogem®, sold by SPI Pharma Group (New Castle, Del.), are freeze-dried processed forms of mannitol and sorbitol, respectively. Typically, the compositions of the present invention comprise from about 25% to about 90% by weight of the binder, and preferably from about 50% to about 80%. However, one skilled in the art will appreciate that the compositions of the present invention can be made without any binders, e.g., to produce a highly friable dosage form.

Non-limiting examples of gum bases include materials selected from among the many water-insoluble and saliva-insoluble gum base materials known in the art. For example, in some instances, the gum base comprises at least one hydrophobic polymer and at least one hydrophilic polymer. Non-limiting examples of suitable hydrophobic and hydrophilic polymers for gum bases include both natural and synthetic polymers such as elastomers, rubbers, and combinations thereof. Examples of suitable natural polymers include, without limitation, substances of plant origin such as chicle, jelutong, gutta percha, crown gum, and combinations thereof. Examples of suitable synthetic polymers include elastomers such as butadiene-styrene copolymers, isobutylene and isoprene copolymers (e.g., "butyl rubber"), polyethylene, polyisobutylene, polyvinylester (e.g., polyvinyl acetate and polyvinyl acetate phthalate), and combinations thereof. In other instances, the gum base comprises a mixture of butyl rubber (i.e., isobutylene and isoprene copolymer), polyisobutylene, and optionally, polyvinylacetate (e.g., having a molecular weight of approximately 12,000). Typically, the gum base comprises from about 25% to about 75% by weight of these polymers, and preferably from about 30% to about 60%.

The compositions of the present invention can additionally include lubricating agents; wetting agents; emulsifying agents; solubilizing agents; suspending agents; preserving agents such as methyl-, ethyl-, and propyl-hydroxy-benzoates, butylated hydroxytoluene, and butylated hydroxyanisole; sweetening agents; flavoring agents; coloring agents; and disintegrating agents such as crospovidone as well as croscarmellose sodium and other cross-linked cellulose polymers.

Lubricating agents can be used to prevent adhesion of the dosage form to the surface of the dies and punches, and to reduce inter-particle friction. Lubricating agents may also facilitate ejection of the dosage form from the die cavity and improve the rate of granulation flow during processing. Examples of suitable lubricating agents include, without limitation, magnesium stearate, calcium stearate, zinc stearate, stearic acid, sodium stearyl fumarate, simethicone, silicon dioxide, talc, hydrogenated vegetable oil, polyethylene glycol, mineral oil, and combinations thereof. The compositions of the present invention can comprise from about 0% to about 10% by weight of the lubricating agent, and preferably from about 1% to about 5%.

Sweetening agents can be used to improve the palatability of the composition by masking any unpleasant tastes it may have. Examples of suitable sweetening agents include, without limitation, compounds selected from the saccharide family such as the mono-, di-, tri-, poly-, and oligosaccharides; sugars such as sucrose, glucose (corn syrup), dextrose, invert sugar, fructose, maltodextrin, and polydextrose; saccharin and salts thereof such as sodium and calcium salts; cyclamic acid and salts thereof; dipeptide sweeteners; chlorinated sugar derivatives such as sucralose and dihydrochalcone; sugar alcohols such as sorbitol, sorbitol syrup, mannitol, xylitol, hexa-resorcinol, and the like, and combinations thereof. Hydrogenated starch hydrolysate, and the potassium, calcium, and sodium salts of 3,6-dihydro-6-methyl-1-1,2,3-oxathiazin-4-one-2,2-dioxide may also be used. Of the foregoing, sorbitol, mannitol, and xylitol, either alone or in combination, are preferred sweetening agents. The compositions of the present invention can comprise from about 0% to about 80% by weight of the sweetening agent, preferably from about 5% to about 75%, and more preferably from about 25% to about 50%.

Flavoring agents can also be used to improve the palatability of the composition. Examples of suitable flavoring agents include, without limitation, natural and/or synthetic (i.e., artificial) compounds such as peppermint, spearmint, wintergreen, cinnamon, menthol, cherry, strawberry, watermelon, grape, banana, peach, pineapple, apricot, pear, raspberry, lemon, grapefruit, orange, plum, apple, fruit punch, passion fruit, chocolate (e.g., white, milk, dark), vanilla, caramel, coffee, hazelnut, combinations thereof, and the like. Coloring agents can be used to color code the composition, for example, to indicate the type and dosage of the therapeutic agent therein. Suitable coloring agents include, without limitation, natural and/or artificial compounds such as FD & C coloring agents, natural juice concentrates, pigments such as titanium oxide, silicon dioxide, and zinc oxide, combinations thereof, and the like. The compositions of the present invention can comprise from about 0% to about 10% by weight of the flavoring and/or coloring agent, preferably from about 0.1% to about 5%, and more preferably from about 2% to about 3%.

When the dosage form is a chewing gum, the composition can comprise zolpidem or a pharmaceutically acceptable salt thereof ("therapeutic agent"), a carrier or excipient such as a gum base, a pH-adjusting agent or buffer system, and optionally a protecting agent. The chewing gum composition may further comprise lubricating agents, wetting agents, emulsifying agents, solubilizing agents; suspending agents, preserving agents, sweetening agents, flavoring agents, and coloring agents. Typically, the chewing gum composition comprises less than about 5 mg (e.g., from about 0.5 mg to about 4.75 mg, from about 1.5 mg to about 2.5 mg, from about 3.0 mg to about 3.75 mg, etc.) of zolpidem or a salt thereof. One skilled in the art understands that the foregoing amounts will vary depending upon the particular source of zolpidem utilized, the amount of zolpidem desired in the final formulation, as well as on the particular release rate of zolpidem desired. In certain instances, the buffer system of the chewing gum composition provides a final salivary pH in excess of at least about 7.8, preferably at least about 8.5, and more preferably at least about 9 (e.g., about 9-11). The chewing gum composition typically comprises from about 20% to about 95% by weight of the gum base, more typically from about 30% to about 85%, and most typically from about 50% to about 70% of the gum base.

The chewing gum composition may further comprise a protecting agent. The protecting agent coats at least part of the therapeutic agent, typically upon the mixing of the two agents. The protecting agent may be mixed with the therapeutic agent in a ratio of from about 0.1 to about 100 by weight, preferably in a ratio of from about 1 to about 50, and more preferably in a ratio of from about 1 to about 10. Without being bound to any particular theory, the protecting agent reduces the adhesion between the therapeutic agent and the gum base so that the therapeutic agent may be more easily released from the gum base. In this way, the therapeutic agent may be delivered across the mucous membranes of the oral cavity within about 5 to about 20 minutes of chewing, preferably within about 10 minutes of chewing. A variety of different protecting agents may be used. Examples of suitable protecting agents include, without limitation, calcium stearate, glycerin monostearate, glyceryl behenate, glyceryl palmitostearate, hydrogenated castor oil, hydrogenated vegetable oil type I, light mineral oil, magnesium lauryl sulfate, magnesium stearate, sodium stearyl fumarate, mineral oil, poloxamer, polyethylene gycol, sodium benzoate, sodium chloride, sodium lauryl sulfate, stearic acid, cab-o-sil, talc, zinc stearate, and combinations thereof.

The gum base may additionally include plasticizers such as softeners or emulsifiers. Such plasticizers may, for example, help reduce the viscosity of the gum base to a desirable consistency and improve its overall texture and bite. Plasticizers may also facilitate the release of the therapeutic agent upon mastication. Non-limiting examples of plasticizers include lecithin, mono- and diglycerides, lanolin, stearic acid, sodium stearate, potassium stearate, glycerol triacetate, glycerol monostearate, glycerin, and combinations thereof. The gum base typically comprises from about 0% to about 20% by weight of the plasticizer, and more typically from about 5% to about 15%.

The gum base may further comprise waxes such as beeswax and microcrystalline wax, fats or oils such as soybean and cottonseed oil, and combinations thereof. Typically, the gum base comprises from about 0% to about 25% by weight of these waxes and oils, and more typically comprises from about 15% to about 20%.

In addition, the gum base may further comprise one or more elastomeric solvents such as rosins and resins. Non-limiting examples of such solvents include methyl, glycerol, and pentaerythritol esters of rosins, modified rosins such as hydrogenated, dimerized or polymerized rosins, or combinations thereof (e.g., pentaerythritol ester of partially hydrogenated wood rosin, pentaerythritol ester of wood rosin, glycerol ester of wood rosin, glycerol ester of partially dimerized rosin, glycerol ester of polymerized rosin, glycerol ester of tall oil rosin, glycerol ester of wood rosin and partially hydrogenated wood rosin and partially hydrogenated methyl ester of rosin such as polymers of alpha-pinene or beta-pinene, terpene resins including polyterpene, and combinations thereof). Typically, the gum base comprises from about 0% to about 75% by weight of the elastomeric solvent, and more typically less than about 10%.

The gum base may further comprise a filler material to enhance the chewability of the final chewing gum composition. Fillers that are substantially non-reactive with other components of the final chewing gum formulation are preferable. Examples of suitable fillers include, without limitation, calcium carbonate, magnesium silicate (i.e., talc), dicalcium phosphate, metallic mineral salts (e.g., alumina, aluminum hydroxide, and aluminum silicates), and combinations thereof. Typically, the gum base comprises from about 0% to about 30% by weight of the filler, and more typically from about 10% to about 20%.

One skilled in the art will appreciate that the gum base need not be prepared from its individual components. For example, the gum base can be purchased with the desired ingredients contained therein, and can be modified to include additional agents. Several manufacturers produce gum bases suitable for use with the described chewing gum compositions. Examples of such gum bases include, without limitation, Pharmagum™ M, S, or C(SPI Pharma Group; New Castle, Del.). In general, Pharmagum™ comprises a mixture of gum base, sweetening agent, plasticizer, and sugar.

In certain instances, the chewing gum composition includes a therapeutic agent centerfill. A centerfill may be particularly suitable when immediate release of the therapeutic agent is preferred. In addition, encapsulating the therapeutic agent in a centerfill may help to mask any undesirable taste that the therapeutic agent may have. In these instances, the gum base surrounds, at least in part, a centerfill. The centerfill comprises at least one therapeutic agent, and may be a liquid or semi-liquid material. The centerfill material can be a synthetic polymer, a semi-synthetic polymer, low-fat, or fat-free and contain one or more sweetening agents, flavoring agents, coloring agents, and/or scenting agents. Preferably, the centerfill includes a buffer system as described herein. Methods for preparing a centerfill chewing gum are described, for example, in U.S. Pat. No. 3,806,290.

The chewing gum compositions can have any desired shape, size, and texture. For example, the chewing gum can have the shape of a stick, tab, gumball, and the like. Similarly, the chewing gum can be any desirable color. For example, the chewing gum can be any shade of red, blue, green, orange, yellow, violet, indigo, and mixtures thereof, and can be color coded to indicate the type and dosage of the therapeutic agent therein. The chewing gum can be individually wrapped or grouped together in pieces for packaging by methods well known in the art.

When the dosage form is a tablet such as a dissolving tablet or chewable tablet, the composition can comprise zolpidem or a pharmaceutically acceptable salt thereof, a carrier or excipient such as a binder, and a pH-adjusting agent or buffer system. The tablet composition may further comprise protecting agents, lubricating agents, wetting agents, emulsifying agents, solubilizing agents; suspending agents, preserving agents, sweetening agents, flavoring agents, coloring agents, and disintegrating agents. Typically, the tablet compositions of the present invention comprise less than about 5 mg (e.g., from about 0.5 mg to about 4.75 mg, from about 1.5 mg to about 2.5 mg, from about 3.0 mg to about 3.75 mg, etc.) of zolpidem or a salt thereof. One skilled in the art understands that the foregoing amounts will vary depending upon the particular source of zolpidem utilized, the amount of zolpidem desired in the final formulation, as well as on the particular release rate of zolpidem desired. In certain instances, the buffer system of the tablet compositions provide a final salivary pH in excess of at least about 7.8, preferably at least about 8.5, and more preferably at least about 9 (e.g., about 9-11).

In certain embodiments, the tablet is a dissolving tablet such as a slow-dissolving or quick-dissolving tablet that is dissolved by a subject's saliva, without the need for chewing. For example, a dissolving tablet placed on the subject's tongue can be used for buccal delivery of the therapeutic agent. Alternatively, a dissolving tablet placed underneath the subject's tongue can be used for sublingual delivery of the therapeutic agent. This type of dosage form may be particularly desirable for pediatric and geriatric patients, since small children and aged individuals often have difficulty chewing certain items. Typically, the dissolving tablet is formulated to dissolve within about 1 to about 15 minutes, preferably within about 2 to about 10 minutes, e.g., within about 2, 3, 4, 5, 6, 7, 8, 9, or 10 minutes, following administration. One skilled in the art will understand that quick-dissolving tablets dissolve faster than slow-dissolving tablets, which are typically dissolved gradually rather than rapidly by a subject's saliva. In a preferred embodiment, the slow-dissolving or quick-dissolving tablet delivers the therapeutic agent across the sublingual mucosa.

In certain other embodiments, the tablet is a chewable tablet that is chewed by a subject and formulated to dissolve either rapidly or gradually. For example, a chewable tablet placed on the subject's tongue can be used for buccal delivery of the therapeutic agent. During chewing, the chewable tablet can be moved around within the mouth and can sometimes be parked between the gums and the cheeks or underneath the tongue. As a result, at least a portion of the therapeutic agent contained within a chewable tablet may also be delivered sublingually (i.e., across the sublingual mucosa). Typically, the chewable tablet is formulated to dissolve within about 1 to about 15 minutes, preferably within about 2 to about 10 minutes, e.g., within about 2, 3, 4, 5, 6, 7, 8, 9, or 10 minutes, following administration.

As described above, the dissolving and chewable tablets of the present invention are typically formulated to dissolve within about 1 to about 15 minutes following administration. However, while these time frames are amenable to maximum exposure of the therapeutic agent to the oral mucosa (e.g., to the sublingual and/or buccal mucosa), they are not always amenable to user compliance (e.g., users may swallow too frequently and, therefore, hinder maximal transmucosal absorption). Consequently, in certain instances, it may be desirable to strike a balance between patient compliance and maximum exposure time of the therapeutic agent to the oral mucosa. This can be accomplished, for example, by reducing the tablet size (e.g., from about 700-800 mg to about 200-300 mg or about 100-350 mg) without reducing the concentration or amount per unit dose of the buffer system or the therapeutic agent. In addition, subtle changes to the tablet formulation such as, for example, replacing one flavoring agent for another (e.g., chocolate for spearmint) or replacing one binder or sweetening agent for another (e.g., lactose for mannitol or sorbitol) may be used to reduce salivation.

The carrier or excipient present in the tablets of the present invention is typically a binder that is useful in keeping the tablet in a semi-solid state, and may be a solid or a liquid, and may for example be a high-melting point fat or waxy material. Materials suitable as binders are discussed in detail above and may be used alone or in combination in the tablet compositions of the present invention. In addition, binders such as mannitol, sorbitol, lactose, sucrose, and inositol can impart properties to the tablet that permit or enhance its disintegration in the mouth.

The tablet composition may also comprise one or more elastomeric solvents such as rosins and resins. Non-limiting examples of such solvents are discussed in detail above and may be used alone or in combination in the tablet compositions of the present invention. In addition, the tablet composition may further comprise waxes such as beeswax and microcrystalline wax, fats or oils such as soybean and cottonseed oil, and combinations thereof. Moreover, the tablet composition may additionally include plasticizers such as softeners or emulsifiers. Such plasticizers may, for example, help reduce the viscosity of the salivary solution of the dissolved tablet to a desirable consistency and improve its overall texture and bite and help facilitate the release of the therapeutic agent. Non-limiting examples of such plasticizers are discussed in detail above and may be used alone or in combination in the tablet compositions of the present invention.

In certain instances, the tablet composition includes a therapeutic agent centerfill, e.g., as described above. In certain other instances, the tablet composition of the present invention is multilayered. In this way, the dissolving or chewable tablet can be designed to provide more than one therapeutic agent. For example, with a bi-layered tablet, the first layer can contain zolpidem or a salt thereof and the second layer can contain the same or different hypnotic agent or a non-hypnotic agent. Typically, the first layer comprises the dissolving or chewable portion of the tablet, and the second (i.e., subsequent) layer is coated by the first layer. This type of formulation may be particularly suitable when immediate release of zolpidem, followed by gastrointestinal absorption of a second therapeutic agent, is desirable. Gastrointestinal absorption of the second therapeutic agent may be desirable, for example, in order to mitigate co-morbid symptoms or to sustain the therapeutic benefit of zolpidem in the dissolving or the chewable portion of the tablet. Alternatively, the second layer is present as a layer lateral to the first layer. The second layer typically comprises at least one therapeutic agent, and can also comprise one or more sweetening agents, flavoring agents, coloring agents, and scenting agents as described above. In some instances, the second layer further includes a buffer system as described herein.

In still other instances, the combination of zolpidem or a salt thereof with other hypnotic agents and/or non-hypnotic agents need not take the form of a multilayered tablet, but instead comprises a single homogenous tablet layer. This type of formulation may also be used in the case where gastrointestinal absorption of at least one therapeutic agent is desirable. In this case, the relative extent of ionization of the two or more therapeutic agents determines how they are to be absorbed. For example, those therapeutic agents that are un-ionized are absorbed through the oral mucosa, while the ionized agents are swallowed for gastrointestinal absorption.

The tablet compositions can have any desired shape, size, and texture. For example, the tablet can have the shape of a stick, tab, pellet, sphere, and the like. Similarly, the tablet can be any desirable color. For example, the tablet can be any shade of red, blue, green, orange, yellow, violet, indigo, and mixtures thereof, and can be color coded to indicate the type and dosage of the therapeutic agent therein. The tablets can be individually wrapped or grouped together in pieces for packaging by methods well known in the art.

When the dosage form is a lozenge or candy, the composition can comprise zolpidem or a pharmaceutically acceptable salt thereof, a carrier or excipient such as a binder, and a pH-adjusting agent or buffer system. The lozenge or candy composition may further comprise protecting agents, lubricating agents, wetting agents, emulsifying agents, solubilizing agents; suspending agents, preserving agents, sweetening agents, flavoring agents, coloring agents, and disintegrating agents. A general discussion of lozenges and candies is provided, e.g., in *Pharmaceutical Dosage Forms, Volume 1: Tablets*, 2$^{nd}$ Ed., Marcel Dekker, Inc., New York, N.Y., pages 75-418 (1989). Typically, the lozenge compositions of the present invention comprise less than about 5 mg (e.g., from about 0.5 mg to about 4.75 mg, from about 1.5 mg to about 2.5 mg, from about 3.0 mg to about 3.75 mg, etc.) of zolpidem or a salt thereof. One skilled in the art understands that the foregoing amounts will vary depending upon the particular source of zolpidem utilized, the amount of zolpidem desired in the final formulation, as well as on the particular release rate of zolpidem desired. In certain instances, the buffer system of the lozenge compositions provides a final salivary pH in excess of at least about 7.8, preferably at least about 8.5, and more preferably at least about 9 (e.g., about 9-11).

In certain embodiments, the lozenge or candy is dissolved by a subject's saliva, without the need for chewing. For example, a lozenge placed on the subject's tongue can be used for buccal delivery of the therapeutic agent. Alternatively, a lozenge placed underneath the subject's tongue can be used for sublingual delivery of the therapeutic agent. This type of dosage form may be particularly desirable for pediatric and geriatric patients, since small children and aged individuals often have difficulty chewing certain items. Typically, the lozenge is formulated to dissolve within about 1 to about 15 minutes, preferably within about 2 to about 10 minutes, e.g., within about 2, 3, 4, 5, 6, 7, 8, 9, or 10 minutes, following administration. In a preferred embodiment, the lozenge or candy delivers the therapeutic agent across the sublingual mucosa.

As described above, the lozenges the present invention are typically formulated to dissolve within about 1 to about 15 minutes following administration. However, while these time frames are amenable to maximum exposure of the therapeutic agent to the oral mucosa (e.g., to the sublingual and/or buccal mucosa), they are not always amenable to user compliance (e.g., users may swallow too frequently and, therefore, hinder maximal transmucosal absorption). Consequently, in certain instances, it may be desirable to strike a balance between patient compliance and maximum exposure time of the therapeutic agent to the oral mucosa. This can be accomplished, for example, by reducing the lozenge size (e.g., from about 700-800 mg to about 200-300 mg or about 100-350 mg) without reducing the concentration or amount per unit dose of the buffer system or the therapeutic agent. In addition, subtle changes to the lozenge formulation such as, for example, replacing one flavoring agent for another (e.g., chocolate for spearmint) or replacing one binder or sweetening agent for another (e.g., lactose for mannitol or sorbitol) may be used to reduce salivation.

The carrier or excipient present in the lozenges of the present invention is typically a binder that is useful in keeping the lozenge in a semi-solid state, and may be a solid or a liquid, and may for example be a high-melting point fat or waxy material. Materials suitable as binders are discussed in detail above and may be used alone or in combination in the lozenge compositions of the present invention. In addition, binders such as mannitol, sorbitol, lactose, sucrose, and inositol can impart properties to the lozenge that permit or enhance its disintegration in the mouth.

The lozenge composition may also comprise one or more elastomeric solvents such as rosins and resins. Non-limiting examples of such solvents are discussed in detail above and may be used alone or in combination in the lozenge compositions of the present invention. In addition, the lozenge composition may further comprise waxes such as beeswax and microcrystalline wax, fats, or oils such as soybean and cottonseed oil, and combinations thereof. Moreover, the lozenge composition may additionally include plasticizers such as softeners or emulsifiers. Such plasticizers may, for example, help reduce the viscosity of the salivary solution of the dissolved lozenge to a desirable consistency and improve its overall texture and bite and help facilitate the release of the therapeutic agent. Non-limiting examples of such plasticizers are discussed in detail above and may be used alone or in combination in the lozenge compositions of the present invention.

In other embodiments, the lozenge composition includes a therapeutic agent centerfill, is multilayered, or comprises a single homogenous lozenge layer, e.g., as described in detail above.

The lozenge compositions can have any desired shape, size, and texture. For example, the lozenge can have the shape of a stick, tab, pellet, sphere, and the like. Similarly, the lozenge can be any desirable color. For example, the lozenge can be any shade of red, blue, green, orange, yellow, violet, indigo, and mixtures thereof, and can be color coded to indicate the type and dosage of the therapeutic agent therein. The lozenges can be individually wrapped or grouped together in pieces for packaging by methods well known in the art.

In a preferred embodiment, the average particle size of the drug in the compositions described herein is about 20 microns, as compared to a typical average drug particle size of from about 75 to about 100 microns. In another preferred embodiment, the average particle size of the drug in the compositions described herein is less than or equal to the average particle size of the carrier ingredients (e.g., gum base, binders, etc.).

Typically, the pharmaceutical compositions are suitable for buccal or sublingual administration of zolpidem in the low doses provided herein. Compositions suitable for buccal or sublingual administration of zolpidem are those that provide absorption in the buccal cavity of at least about 10%, 20%, or 25% of the dosage of zolpidem in the composition. This amount is generally at least twice the amount of buccal absorption that could be expected for a tablet designed to be swallowed for absorption of the active agent in the gut. Additionally, the time to $C_{max}$ is reduced for such compositions relative to tablets or capsules designed to deliver zolpidem in the gut. The compositions suitable for buccal or sublingual administration of zolpidem in low doses, as noted above, are sufficient to reduce the time to $C_{max}$, enhancing the early effect of zolpidem and increase plasma levels of zolpidem, generally two-fold or more during the first 20 minutes after administration, relative to tablets or capsules designed for delivery in the gut (e.g., to be swallowed immediately upon ingestion).

Typically, the compositions that are suitable for the treatment of MOTN insomnia following buccal or sublingual administration have a unique and discriminatory dissolution profile. Such a dissolution method relies on modified USP method II dissolution procedure and where the pH of the dissolution medium is 6.8, which approximates the pH of the saliva. The method is considered to be a modification as the volume of the medium is reduced to 500 ml from 1 liter and the paddle speed for dissolution is reduced to 15 rpm from a typical speed of 50 or more rpm. This method is sufficiently sensitive to discriminate a 2 to 3 minute dissolution tablet from a tablet that would normally take 5 minutes or more to dissolve in the mouth. Typically, a tablet that would dissolve in the mouth in 3 minutes or less would dissolve more rapidly under experimental conditions of modified USP method II than a tablet that takes 5 or more minutes to dissolve in the mouth (see, Tables 1-2 below)

TABLE 1

Exploratory dissolution profiles of 3 and 5 minute dissolution of zolpidem lozenges using the modified USP dissolution method II. (500 ml of pH 6.8 phosphate buffer at a 37° C. and paddle speed of 15 rpm).

| | Lozenge | | | |
|---|---|---|---|---|
| | "3 minute" dissolution prototype | | "5 minute" dissolution prototype | |
| Time (min) | Dissolution | RSD* | Dissolution | RSD* |
| 5 | 28.60% | 5% | 8.70% | 12.00% |
| 10 | 58.40% | 10% | 20.00% | 11.30% |
| 20 | 79.00% | 20% | 38.30% | 11.40% |

*Relative standard deviation

TABLE 2

Illustrative dissolution profiles of 1, 3.5, and 10 mg "3 minute" zolpidem lozenges using the modified USP dissolution method II. (500 ml of pH 6.8 phosphate buffer at a 37° C. and paddle speed of 15 rpm).

| Lozenge | 1 mg "3 minute" dissolution prototype | | 3.5 mg "3 minute" dissolution prototype | | 10 mg "3 minute" dissolution prototype | |
|---|---|---|---|---|---|---|
| Time (min) | Dissolution | RSD | Dissolution | RSD | Dissolution | RSD |
| 5 | 28.70% | 11.60% | 42.40% | 11.14% | 28.60% | 19.90% |
| 10 | 46.90% | 9.30% | 70.20% | 6.53% | 58.40% | 10.40% |
| 15 | 60.40% | 6.70% | 81.00% | 7.23% | | |
| 20 | 70.50% | 5.20% | 84.30% | 7.14% | 79.00% | 5.10% |

In some embodiments, the compositions of the present invention provide complete buccal and/or sublingual dissolution in about 2 minutes or less following administration. The quick-dissolving tablets of the present invention usually provide complete buccal and/or sublingual dissolution in less than about 0.5 minutes, alternatively in less than about 1 minute, alternatively in less than about 1.5 minutes, alternatively in less than about 2 minutes, alternatively in less than about 2.5 minutes, alternatively in less than about 3 minutes, alternatively in less than about 4 minutes, alternatively in less than about 5 minutes, or alternatively in less than about 6 minutes.

Generally, the compositions described herein comprise a binary or a ternary buffer system, the system comprised of at least one proton donating (acidic) component and at least one proton accepting (basic) component. The components of the buffer system are selected such that their buffering capacity is greatest (the buffer system has a pK value) at a pH of from about 7.2-11.0, usually at a pH of about, for example, 7.2, 7.6, 7.8, 8.0, 8.3, 8.5, 8.8, 9.0, 9.4, 9.5, 9.6, 9.7, or 9.8.

In preferred embodiments, the binary buffer system raises the pH of saliva to a pH greater than about 7.2, 7.6, 7.8, 8.0, 8.3, 8.5, or 8.8, irrespective of the starting pH of saliva. In other embodiments, the binary buffer system raises the pH of saliva to a pH greater than about 9.0, 9.4, 9.5, 9.6, 9.7, or 9.8 (e.g., about 9-11), irrespective of the starting pH of saliva.

Preferably, the buffer system comprises a carbonate and a bicarbonate component. For example, the carbonate salt can be selected from the group consisting of sodium carbonate, potassium carbonate, calcium carbonate, ammonium carbonate, and magnesium carbonate. The bicarbonate salt can be selected from the group consisting of sodium bicarbonate, potassium bicarbonate, calcium bicarbonate, ammonium bicarbonate, and magnesium bicarbonate. In a preferred embodiment, the binary buffer system comprises sodium carbonate and sodium bicarbonate. In another preferred embodiment, the sodium bicarbonate is dessicant-coated sodium bicarbonate. The cations of the carbonate and the bicarbonate components can be the same or different.

The concentration of each buffer system component is tailored such that the final salivary pH is achieved and sustained for a period of time, e.g., for at least about 2 minutes, at least about 5 minutes, at least about 10 minutes, at least about 20 minutes, or at least about 60 minutes. This typically involves a sensory and safety trial and error type of procedure of adding various amounts of each buffer system component and then measuring the final pH over time. In this way, selection of an appropriate weight ratio for each buffer system component can be determined. For example, the weight ratio of carbonate salt to bicarbonate salt can be from about 1:10 to about 10:1, preferably from about 1:5 to about 5:1, more preferably from about 1:4 to about 4:1 or from about 1:3 to about 3:1, and still more preferably from about 1:2 to about 2:1.

In some embodiments, the amount of bicarbonate salt is greater than or equal to the amount of carbonate salt, and the weight ratio of carbonate salt to bicarbonate salt is from about 1:1 to about 1:10, preferably from about 1:1 to about 1:5, and more preferably from about 1:1 to about 1:2, e.g., 1:1, 1:1.1, 1:1.2, 1:1.3, 1:1.4, 1:1.5, 1:1.6, 1:1.7, 1:1.8, 1:1.9, or 1:2.

Alternatively, the amount of bicarbonate salt is less than or equal to the amount of carbonate salt, and the weight ratio of carbonate salt to bicarbonate salt is from about 1:1 to about 10:1, preferably from about 1:1 to about 5:1, and more preferably from about 1:1 to about 2:1, e.g., 1:1, 1.1:1, 1.2:1, 1.3:1, 1.4:1, 1.5:1, 1.6:1, 1.7:1, 1.8:1, 1.9:1, or 2:1. In some embodiments, the combined amount of carbonate salt and bicarbonate salt is greater than or equal to the amount of zolpidem, and the weight ratio of carbonate salt and bicarbonate salt to zolpidem is preferably from about 1:1 to about 10:1, e.g., 1:1, 2:1, 3:1, 4:1, 5:1, 6:1, 7:1, 8:1, 9:1, or 10:1. Alternatively, the combined amount of carbonate salt and bicarbonate salt is less than or equal to the amount of zolpidem, and the weight ratio of carbonate salt and bicarbonate salt to zolpidem is preferably from about 1:1 to about 1:10, e.g., 1:1, 1:2, 1:3, 1:4, 1:5, 1:6, 1:7, 1:8, 1:9, or 1:10.

In some embodiments, the binary buffer system used in compositions described above comprises a carbonate salt such as sodium carbonate and a bicarbonate salt such as sodium bicarbonate, wherein the carbonate salt and the bicarbonate salt are in a carbonate:bicarbonate ratio of from about 1:1.0 to about 1:1.4 by weight, or alternatively from about 1:1.0 to about 1:1.2 by weight.

In other embodiments, the bicarbonate can be used by itself to promote selective absorption of zolpidem.

Other buffer systems are suitable for use in the compositions of the present invention, in addition to or in substitution of a carbonate and bicarbonate buffer system. For example, in an alternative embodiment, the buffer system comprises a carbonate salt or a bicarbonate salt and a second buffering agent such as a metal oxide, a citrate salt, a phosphate salt, a borate salt, an ascorbate salt, an acetate salt, and alkaline starch. In another alternative embodiment, the buffer system comprises a metal oxide and a citrate, phosphate, or borate salt. In yet another alternative embodiment, the buffer system is a ternary buffer system comprising a carbonate salt, a bicarbonate salt, and a third buffering agent such as a metal oxide, a citrate salt, a phosphate salt, a borate salt, an ascorbate salt, an acetate salt, and alkaline starch. In still yet another alternative embodiment, the buffer system comprises a carbonate salt or a bicarbonate salt and two or more buffering agents selected from the group consisting of a metal oxide, a citrate salt, a phosphate salt, and a borate salt.

In still other embodiments, the pharmaceutical compositions comprise a carrier comprising at least one binder and at least one disintegrating agent in such relative proportion to provide a buccal or sublingual dissolution time of about 5 minutes or less, preferably about 2 minutes or less, following administration. Preferably, the ratio of the binder to the disintegrating agent is from about 0.1 to about 10.0, more preferably from about 0.1 to about 1.0, and most preferably from about 0.26 to about 0.79. However, one skilled in the art will appreciate that the compositions of the present invention can be made without any binders, e.g., to produce a highly friable dosage form.

In a preferred embodiment, the zolpidem is delivered across an oral mucosa selected from the group consisting of the sublingual mucosa, the buccal mucosa, and a combination thereof. In a particularly preferred embodiment, the composition is administered sublingually so that the zolpidem is delivered across the sublingual mucosa.

In preferred embodiments of the present invention, the zolpidem is formulated in a binary buffer system comprising sodium carbonate and sodium bicarbonate. Such compositions are preferably formulated in the form of a lozenge, candy, or dissolving tablet (e.g., slow-dissolving tablet or quick-dissolving tablet) for sublingual administration. As a result, upon sublingual administration, zolpidem is delivered across the sublingual mucosa. In another preferred embodiment, the sodium bicarbonate is dessicant-coated sodium bicarbonate. A combined weight percent of sodium carbonate and sodium bicarbonate that is greater than or equal to the weight percent of zolpidem is also preferred.

In some embodiments, the composition comprises from about 0.4, 0.45, or 0.5 to about 1.5, 1.6, 1.7, or 1.8 weight percent zolpidem; from about 6.0 to about 10.0 weight percent sodium carbonate; and from about 9.0 to about 13.0 weight percent dessicant-coated sodium bicarbonate. In a preferred embodiment, the composition comprises about 0.47, 0.8, or 1.7 weight percent zolpidem; about 8.0 weight percent sodium carbonate; and about 11.0 weight percent dessicant-coated sodium bicarbonate. Such compositions are preferably in the form of a lozenge or candy with a mass of from about 100 to about 300 mg, e.g., about 100, 110, 120, 130, 140, 150, 160, 170, 180, 190, 200, 210, 220, 230, 240, 250, 260, 270, 280, 290, and 300 mg. The lozenges or tablets dissolve in a subject's mouth at a very rapid rate, e.g., within about 2-3 minutes following administration.

In certain other instances, the composition comprises from about 0.4, 0.45, or 0.5 to about 1.5, 1.6, 1.7, or 1.8 weight percent zolpidem; from about 5.0 to about 9.0 weight percent sodium carbonate; and from about 7.0 to about 11.0 weight percent sodium bicarbonate. In a preferred embodiment, the composition comprises about 0.47, 0.8, or 1.7 weight percent zolpidem; about 7.0 weight percent sodium carbonate; and about 9.0 weight percent sodium bicarbonate. Such compositions are preferably in the form of a dissolving tablet such as a slow-dissolving tablet or a quick-dissolving tablet of from about 100 to about 300 mg, e.g., about 100, 110, 120, 130, 140, 150, 160, 170, 180, 190, 200, 210, 220, 230, 240, 250, 260, 270, 280, 290, and 300 mg. The quick-dissolving tablets dissolve in a subject's mouth at a rapid rate, e.g., within about 5 minutes following administration, and the slow-dissolving tablets dissolve in a subject's mouth at a slower rate, e.g., within about 10 minutes following administration.

V. Methods

In carrying out the methods of the present invention for treating MOTN insomnia, the appropriate effective dosage to be administered to a subject can be evaluated in an appropriate patient population that has been selected based on factors such as age, weight, the number of hours of time in bed remaining, and/or the ability of a subject to metabolize zolpidem. For example, a dose of about 2 mg to about 5 mg can be administered to a subject who awakens and still has about 4 or 5 hours of time in bed remaining. Similarly, a dose of about 3 mg to about 5 mg can be administered to non-elderly subjects (i.e., subjects younger than 65 years of age) with a normal capacity to metabolize zolpidem. If the subject awakens with about 2-4 hours of time in bed remaining, a dose of about 0.5 mg to about 2.5 mg can be administered. Likewise, subjects with a diminished capacity to metabolize zolpidem (i.e., subjects 65 years of age and older) can be administered a portion of a dose that would be administered to a subject with a normal capacity to metabolize zolpidem, for example, a half-tablet dose. One of skill in the art will appreciate that there can be some variability in the dose provided to some individuals. For example, hepatically-impaired individuals may use a very low dose such as that typically provided for an elderly patient.

Typically, an effective amount of zolpidem is administered to a subject with MOTN insomnia on an as needed basis, i.e., pro re nata. That is, the individual had previously fallen asleep, and the sleep time has been interrupted with at least about 2, 3, 4, or 5 hours of time in bed remaining. Generally, in practicing the present methods, zolpidem is not administered prophylactically, or before initial onset of sleep.

Typically, the methods are carried out by administering a composition of the present invention as described above. Compositions of particular interest for treating MOTN insomnia contain less than about 5 mg of zolpidem or a salt thereof. In certain embodiments, the zolpidem can be administered in a quick-dissolving tablet or lozenge. Efficient delivery of zolpidem can be achieved using a formulation with a binary or a ternary buffer system, for example with carbonate and bicarbonate components, as described above.

Administration of the compositions of the present invention is preferably carried out via any of the accepted modes of administration to the mucous membranes of the oral cavity. Examples of suitable sites of administration within the oral mucosa include, without limitation, the mucous membranes of the floor of the mouth (sublingual mucosa), the cheeks (buccal mucosa), the gums (gingival mucosa), the roof of the mouth (palatal mucosa), the lining of the lips, and combinations thereof. These regions differ from each other with respect to their anatomy, drug permeability, and physiological response to drugs. Preferably, the compositions of the present invention are administered to the sublingual mucosa, buccal mucosa, or a combination thereof.

The oral mucosa, possessing a rich blood supply and suitable drug permeability, is an especially attractive route of administration for systemic drug delivery. Furthermore, delivery of a therapeutic agent across the oral mucosa bypasses hepatic first pass metabolism, avoids enzymatic degradation within the gastrointestinal tract, and provides a more suitable enzymatic flora for drug absorption. As used herein, the term "sublingual delivery" refers to the administration of a therapeutic agent across the mucous membranes lining the floor of the mouth and/or the ventral tongue. The term "buccal delivery" as used herein refers to the administration of a therapeutic agent across the mucous membranes lining the cheeks.

VI. Examples

The following examples are offered to illustrate, but not to limit, the claimed invention.

Example 1

Low Dose Zolpidem Lozenge Compositions

Individuals suffering from middle-of-the-night insomnia are given lozenges containing 0 mg, 1.0 mg, 1.75 mg, or 3.5 mg zolpidem for sublingual delivery that are prepared according to the formulations set forth in Table 3.

TABLE 3

Low dose zolpidem lozenge formulations.

| Component | Quantity (mg/lozenge) Strength | | | | |
|---|---|---|---|---|---|
| | Placebo | 1.0 mg | 1.75 mg | 1.75 mg | 3.5 mg |
| Zolpidem hemitartrate | 0 | 1.0 | 1.75 | 1.75 | 3.5 |
| Pharmaburst ™ B2 Consisting of: mannitol sorbitol crospovidone silicon dioxide | 143 | 142 | 70 | 141.25 | 139.5 |

TABLE 3-continued

Low dose zolpidem lozenge formulations.

| Component | Quantity (mg/lozenge) Strength | | | | |
|---|---|---|---|---|---|
| | Placebo | 1.0 mg | 1.75 mg | 1.75 mg | 3.5 mg |
| Croscarmellose sodium | 10 | 10 | 5 | 10 | 10 |
| Sodium carbonate | 17 | 17 | 8.5 | 17 | 17 |
| Sodium bicarbonate | 23 | 23 | 11.5 | 23 | 23 |
| Natural and artificial spearmint FONA# 913.004 | 6.5 | 6.5 | 3.25 | 6.5 | 6.5 |
| Silicon dioxide | 5.5 | 5.5 | 2.75 | 5.5 | 5.5 |
| Sucralose | 1.5 | 1.5 | 0.75 | 1.5 | 1.5 |
| Magnesium stearate | 3.5 | 3.5 | 1.75 | 3.5 | 3.5 |
| Total lozenge weight | 210 | 210 | 105 | 210 | 210 |

The individuals self-administer one lozenge of the above formulations when their sleep is interrupted and they have at least 2 hours of sleep time remaining. Upon awakening, the individuals provide a subjective self-assessment of any residual sedative effects and are given the following psychomotor and memory tests to evaluate any residual sedative effects: a digit symbol substitution test (DSST), a choice reaction time (CRT), a symbol copy test (SCT), and a Buschke Memory Recall Test.

Individuals receiving a placebo lozenge are generally unable to fall back asleep and therefore do not feel refreshed in the morning. Individuals receiving lozenges containing 1.0 mg, 1.75 mg, or 3.5 mg zolpidem fall asleep within about 20 minutes after self-administration of the lozenge and exhibit no or minimal residual sedative effects as evaluated by subjective self-assessment and any of the above-referenced psychomotor and memory tests.

Example 2

Pharmacokinetic and Pharmacodynamic Investigation of Low Dose Zolpidem Lozenge Compositions This example provides an evaluation of the daytime dose-dependent pharmacokinetic and pharmacodynamic effects of the 1.0 mg, 1.75 mg, and 3.5 mg zolpidem lozenges described in Table 3 above.

SUMMARY

Currently, no medications are available to be used on a pro re nata basis for patients who have middle-of-the-night (MOTN) awakening and who have difficulty falling back asleep. An appropriate therapeutic agent for such insomnia would enable patients to return to sleep rapidly and wake up in the morning without residual effects. This study illustrates, inter alis, that the low dose zolpidem lozenges of the present invention enhance rapid systemic delivery of zolpidem without affecting other pharmacokinetic parameters.

Healthy adults (n=24; mean age=37.6 yrs) participated in this double-blind, placebo-controlled, 4-way crossover study of 2 consecutive days of morning dosing with placebo, or 1 mg, 1.75 mg, or 3.5 mg of the low dose zolpidem lozenges of the present invention. After morning dosing, on Day 1 of each period, pharmacodynamic endpoints (DSST, PVT, VAS-sedation, SCT, and Buschke) were evaluated at pre-dose and at 20 minutes 1, 1.5, 2, 3, 4, and 5 hours post-dose. On Day 2, repeated blood samples for pharmacokinetic assessment were drawn over 12 hours.

Baseline DSST scores (±SE) were 57.6±2.9, 58.0±3.1, 58.4±2.3, and 56.9±2.7 for the placebo, 1 mg, 1.75 mg, and 3.5 mg zolpidem lozenge, respectively. Significant reductions in DSST, scores were found for the 1.75 mg and 3.5 mg zolpidem lozenges at the beginning of 20 minutes (−6.6; p=0.0132 and −14.8; p<0.001, respectively) and lasted for 1.5 hours post-dose. Other endpoints showed results similar to DSST. Mean $T_{max}$ was 36.0, 37.9, and 37.9 minutes for the 1 mg, 1.75 mg, and 3.5 mg zolpidem lozenge, respectively. Zolpidem $C_{max}$ and AUC were dose-proportional. The 1.75 mg and 3.5 mg zolpidem lozenges reached sedation plasma levels (about 20 ng/ml) within 15 minutes, and these levels were maintained for 15 to 240 minutes.

Low dose zolpidem lozenges provide daytime sedative properties at a dose and a $T_{max}$ of less than half of the approved dose of peroral (PO) zolpidem (10 mg) in adults. This study demonstrates that the low dose sublingual zolpidem lozenges of the present invention can be used to shorten sleep onset upon MOTN administration.

Methods

Design

This was a four-way crossover, placebo controlled, randomized double blind study with healthy male (n=13) and female (n=11) volunteers. Each treatment period consisted of two single-dose consecutive treatment days, and each treatment was separated by a wash-out period of 6 days or more. During each period, lozenges were administered approximately 24 hours apart, and the subjects received the same treatment on each day. During each period, in order to avoid any learning or drug-anticipatory response, the pharmacodynamic effects were measured on Day 1 and blood samples drawn on Day 2 for pharmacokinetic assessment.

Pharmacodynamic assessment consisted of measurements of sedation, memory, and vigilance tests. The sedative effects were quantified by a decrease in post- to pre-dose scores on a Digit Symbol Substitution Test (DSST) and self-rated assessment sedation on a Visual Analog Scale (VAS). Vigilance was assessed by an increase in post- to pre-dose scores by measurement of reaction time and number of lapses in reaction to digital stimuli using a computerized Psychomotor Vigilance Test (PVT). A decrease in post- to pre-dose scores on a Buschke Word Recall Test (Buschke) was used for memory effects. Additionally, a Symbol Copy Test (SCT) was used for measurement of simple cognitive function. The results were statistically analyzed using SAS, ANOVA procedures and significance was assessed using Dunnett's test for comparison.

Serial blood samples were drawn for up to 12 hours at pre-dose, 5, 10, 20, 30, and 45 minutes and 1, 2, 2.5, 3, 3.5, 4, 5, 6, 8, and 12 hours. Non-compartmental pharmacokinetic parameters were estimated using the WinNonlin program (Pharsight Corp.; Palo Alto, Calif.). The parameters estimated were AUC and partial AUC, $C_{max}$, $t_{max}$, and $t_{1/2}$.

Additionally, the plasma levels of the 1.0 mg, 1.75 mg, and 3.5 mg zolpidem lozenges were predicted following single compartment first order input and output modeling of data for a 10 mg zolpidem lozenge using the following equation:

$$Ct = D*K01/V/(K01-K10)*\mathrm{EXP}(-K10*T) - \mathrm{EXP}(-K01*T),$$

wherein Ct=predicted plasma concentration, D=dose, V=apparent volume of distribution, T=time, K01=absorption rate constant, and K10=the elimination rate constant. The values for V, K01 and K10 were obtained by fitting the plasma data from the 10 mg zolpidem lozenge (i.e., 3 minute dissolution lozenge swallowed every 2 minutes) to the above equation. Unless otherwise indicated, standard deviation is the variance parameter associated with the mean values.

Results

Pharmacokinetics

Figure 2:
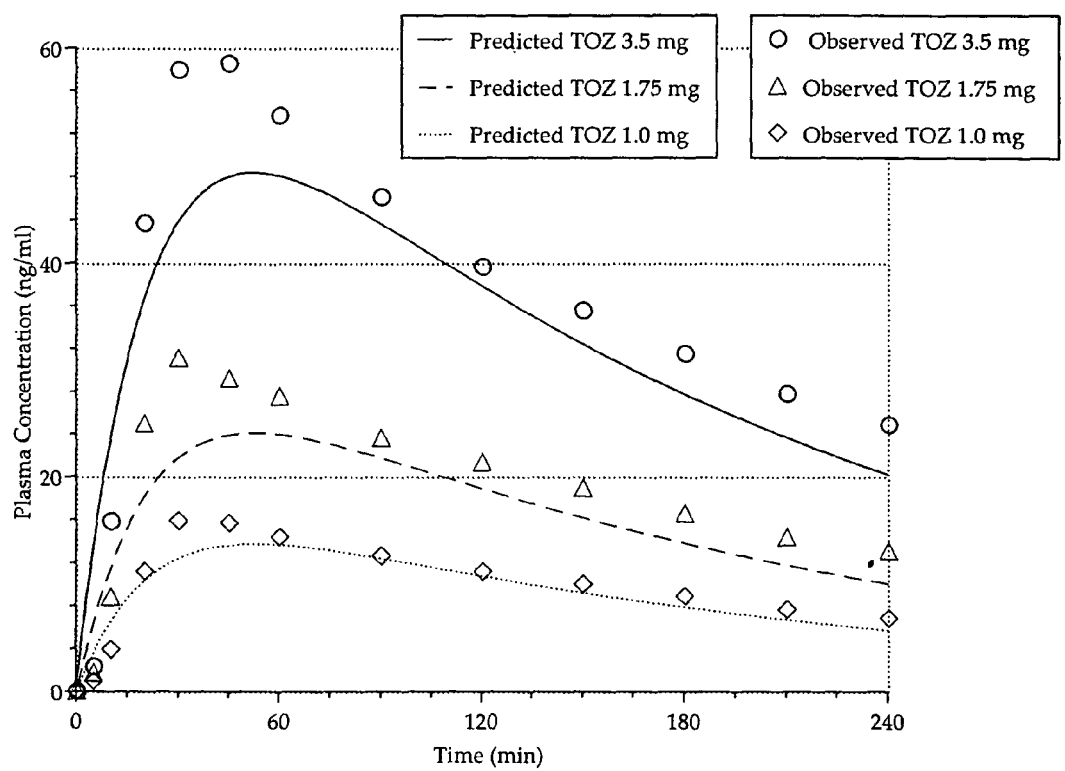
FIG. 2 shows the predicted versus observed plasma profiles of a 1.0 mg, 1.75 mg, and 3.5 mg sublingual zolpidem lozenge of the present invention.

Zolpidem was rapidly absorbed and eliminated from each of the three low dose sublingual lozenge formulations. The plasma profiles of the three lozenge formulations are shown in FIG. 1, and summary statistics of the pharmacokinetic parameters are described in Table 4. Overall, the $t_{max}$ and $C_{max}$ of the three lozenge formulations were significantly shorter and higher, respectively, than the values either predicted by modeling of the 10 mg data (see, FIG. 2) or reported in the literature.

TABLE 4

Mean (% CV) bioavailability parameters of the low dose zolpidem lozenges.

| Dose mg | $C_{max}$ ng/ml | $t_{max}$ min | AUC 0-12 hr ng · hr/ml | AUC 0-20 mn ng · hr/ml | Mean Bioavailability Rate (ng/ml per min) |
|---|---|---|---|---|---|
| 1.0 | 17.77 (33%) | 36 (30%) | 65.31 (40%) | 1.53 (42%) | 0.49 |
| 1.75 | 32.17 (32%) | 37.9 (42%) | 119.54 (40%) | 3.20 (42%) | 0.85 |
| 3.5 | 64.14 (33%) | 37.9 (40%) | 229.42 (40%) | 5.80 (41%) | 1.69 |

In particular, this pharmacokinetic study provided the following key observations:
1. The 3.5 mg lozenge produced a $C_{max}$ of about 64 ng/ml in about 38 minutes with an AUC0-12 hr of about 229 ng·hr/ml. The mean value AUC0-20 min was 5.80 ng·hr/ml.
2. The values of the $C_{max}$ and $t_{max}$ for the 1.75 mg lozenge were about 32 ng/ml and 38 minutes, respectively. The values of AUC0-12 hr and AUC0-20 min were 119.54 and 3.20 ng·hr/ml, respectively.
3. The values of the $C_{max}$ and $t_{max}$ for the 1 mg lozenge were about 18 ng/ml and 36 minutes, respectively. The values of AUC0-12 hr and AUC0-20 min were 65.31 and 1.53 ng·hr/ml, respectively.
4. The observed values of $C_{max}$ of all three lozenge formulations were significantly higher than the values predicted by pharmacokinetic modeling of the 10 mg data.
5. The pharmacokinetics of the three lozenge formulations were proportional to the dose.

Pharmacodynamics

Figure 3:
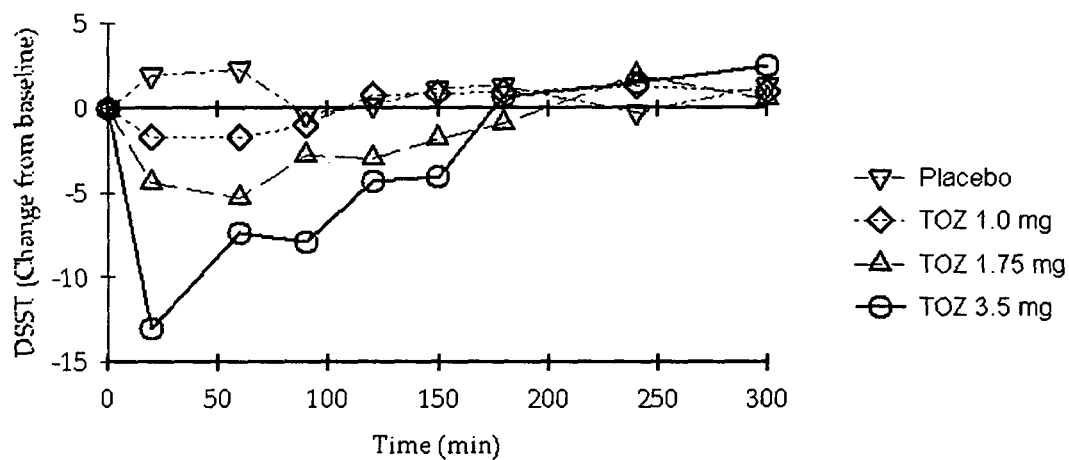
FIG. 3 shows the Digit Symbol Substitution Test (DSST) scores of a 1.0 mg, 1.75 mg, and 3.5 mg sublingual zolpidem lozenge of the present invention as a function of time.

Digit Symbol Substitution Test (DSST): The DSST is an objective measure of sedation. As shown in FIG. 3, the 1.75 mg and 3.5 mg zolpidem lozenges produced peak changes in DSST scores within 20 to 60 minutes of administration, and scores returned to baseline within 3 to 4 hours of administration. These scores were significantly different from baseline for up to about 90 minutes. The DSST scores for the 1 mg zolpidem lozenge were statistically similar to that of the placebo.

Figure 4:
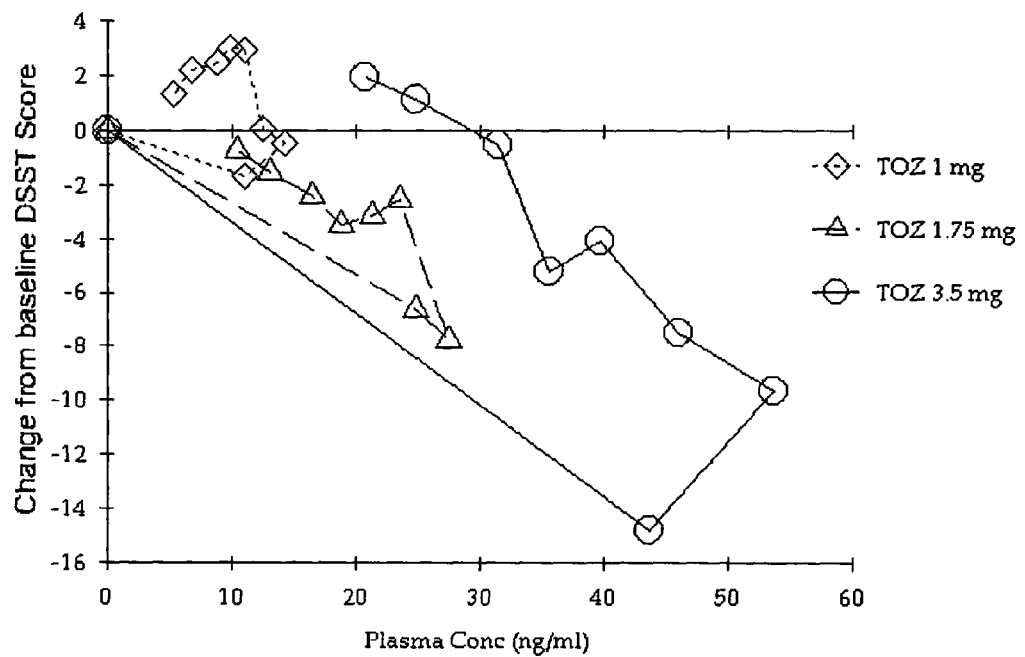
FIG. 4 shows the DSST scores of a 1.0 mg, 1.75 mg, and 3.5 mg sublingual zolpidem lozenge of the present invention as a function of plasma concentration.

FIG. 4 shows that the relationship between plasma levels of the zolpidem lozenges and the DSST response is characterized by an anti-clockwise hysteresis loop, which is typical for sedative-hypnotics. This indicates that the rapid pharmacodynamic effects are primarily due to the rapid bioavailability of the zolpidem present in the lozenges and not due to any changes in the receptor pharmacology of the drug.

Figure 5:
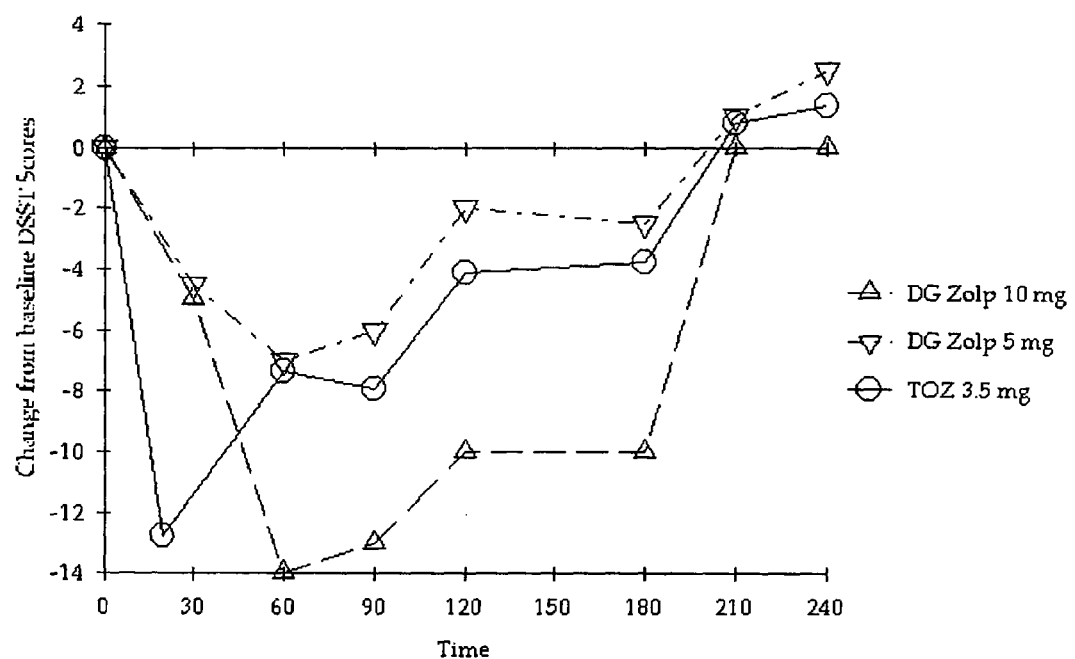
FIG. 5 shows a comparison of DSST scores of a 3.5 mg sublingual zolpidem lozenge of the present invention and 5 mg and 10 mg peroral (PO) Ambien® as reported in the literature.

One of the most surprising findings from the DSST scores for the 3.5 mg zolpidem lozenge is that the sedative response is more rapid than the values reported in the literature for 5 mg and 10 mg peroral (PO) Ambien® (see, Greenblatt et al., *Clin. Pharmacol. Therap.*, 64:553-561 (1998); Greenblatt et al., *Clin. Pharmacol. Therap.*, 64:661-671 (1998)). In particular, FIG. 5 shows that the 3.5 mg zolpidem lozenge was capable of inducing sleep more rapidly than both 5 mg and 10 mg PO Ambien®, but did not cause the excessive sedation associated with 10 mg PO Ambien®.

Figure 6:
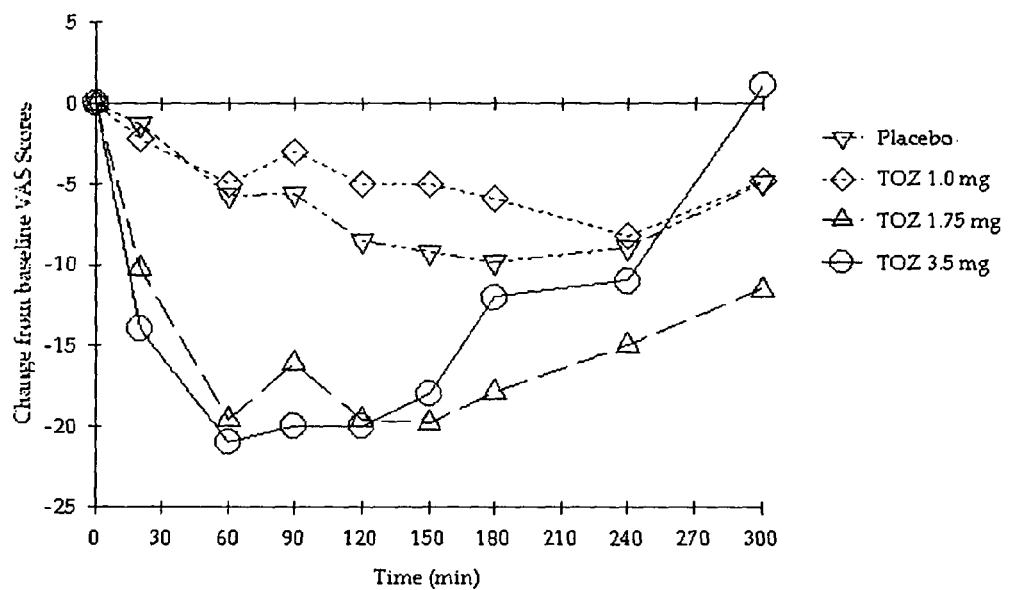
FIG. 6 shows the Visual Analog Scale (VAS) scores of a 1.0 mg, 1.75 mg, and 3.5 mg sublingual zolpidem lozenge of the present invention.

Self-rated assessment of sedation on VAS: Unlike DSST, the subjective sedative effects of the 1.75 mg and 3.5 mg zolpidem lozenges were similar (FIG. 6). The Visual Analog Scale (VAS) scores for these low zolpidem doses were statistically different than placebo for up to 2 hours.

Figure 7:
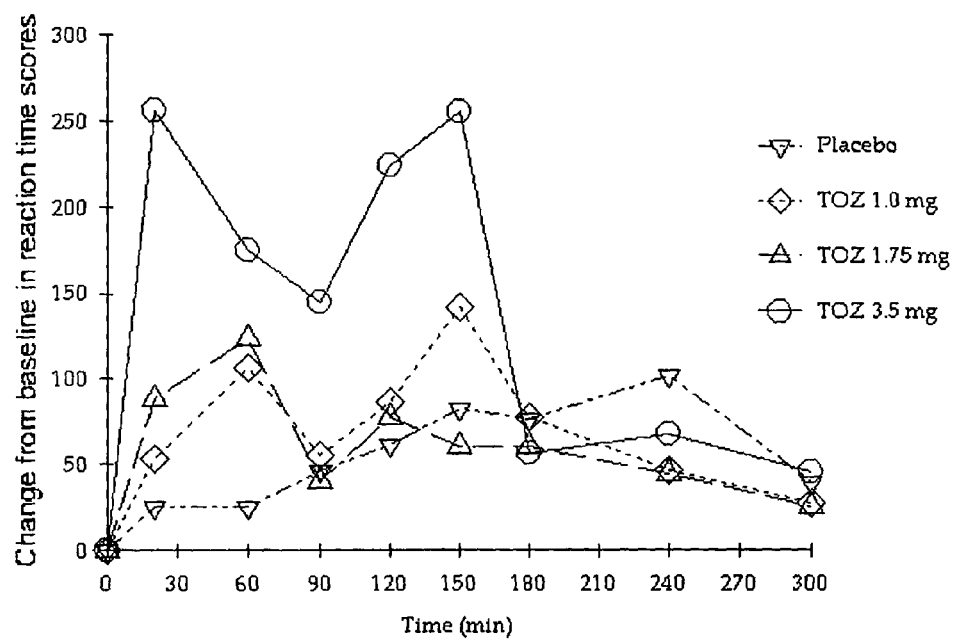
FIG. 7 shows the change in reaction time scores as measured by a Psychomotor Vigilance Test (PVT) of a 1.0 mg, 1.75 mg, and 3.5 mg sublingual zolpidem lozenge of the present invention.

Vigilance changes as measured by PVT: The 3.5 mg zolpidem lozenge also impaired vigilance, as measured by reaction times using a Psychomotor Vigilance Test (PVT). FIG. 7 shows that the reaction time scores for the 3.5 mg zolpidem lozenge were statistically different for up to about 90 minutes.

Memory impairment (Buschke): Except for the significant effect seen at 20 minutes with the 3.5 mg zolpidem lozenge, the drug effects were comparable to that of the placebo.

Simple motor task impairment (SCT): The effects of the three lozenge formulations were comparable to that of the placebo.

CONCLUSIONS

1. Surprisingly, the zolpidem blood levels established at several time points up to 30 mintues after dosing with the 3.5 mg zolpidem lozenge exceeded those reported in the literature for PO Ambien® doses up to and including 10 mg. In fact, the 3.5 mg zolpidem lozenge was superior to 10 mg PO Ambien® (which contains nearly 3 times the dose of zolpidem) because it provided a significantly greater sedative effect at 30 minutes as measured by DSST testing.
2. The $C_{max}$ (maximum plasma concentration) of zolpidem from the low dose zolpidem lozenges was about 30% higher than the values predicted by pharmacokinetic modeling of data for a 10 mg zolpidem lozenge. The mean $C_{max}$ (64 ng/ml) of the 3.5 mg zolpidem lozenge was in the same range as the values reported for 5 mg PO Ambien®. Further, both 1.75 mg and 3.5 mg zolpidem lozenges produced plasma levels at 30 minutes or earlier that have been reported in the literature to produce sedative effects.
3. The low dose zolpidem lozenges achieved maximum plasma concentrations in about 36 to 38 minutes. A $t_{max}$ of about 35 minutes was significantly earlier than the $t_{max}$ of 1 to 1.5 hours typically reported for 5 mg and 10 mg PO zolpidem (Ambien®), eszopiclone (Lunesta™), zaleplon (Sonata®), and remelteon (Rozerem™)
4. The pharmacodynamic data described above demonstrate that the 1.75 mg and 3.5 mg zolpidem lozenges produced rapid sedative-hypnotic effects without the risk of anterograde amnesia or falling in night, which are side-effects typical of higher PO Ambien® doses.
5. The pharmacokinetic and pharmacodynamic response to the low dose zolpidem lozenges was proportional to the dose. Therefore, the pharmacology of zolpidem at a dose range of between about 1 mg to 3.5 mg, unlike that of 5 mg PO Ambien®, is expected to produce a consistent and predictable response.
6. The pharmacodynamic data described above clearly demonstrate the sedative effects of 1.75 mg and 3.5 mg zolpidem lozenge formulations, which included rapid onset of action. In fact, the onset of action and peak effects as defined by both DSST (objective) and VAS (subjective) occurred within 20 minutes. In contrast, 5 mg PO Ambien® produced peak DSST effects in about 60 minutes and the magnitude of the response was only about 50% of that seen with the 3.5 mg zolpidem lozenge. The levels of decline in DSST (surrogate for sedation) scores were comparable to those seen with marketed hypnotics.
7. During the pharmacodynamic portion of the study, low dose zolpidem lozenges containing 1.75 or 3.5 mg zolpidem produced peak sedative effects (as measured by DSST and VAS) within about 20 minutes of dosing.
8. The 3.5 mg zolpidem lozenge also impaired vigilance (as measured by reaction times on PVT). The 1.75 mg zolpidem lozenge had no effect on subjects who were non-elderly adults.
9. None of the doses of zolpidem present in the low dose zolpidem lozenges impaired performance on a memory test (Buschke) or a simple motor task capability test (SCT).

Example 3

Low Dose Zolpidem Tablet Composition

An immediate release peroral (PO) tablet containing a low dose of zolpidem can be prepared according to the formulation set forth in Table 5.

TABLE 5

Low dose zolpidem tablet formulation.

| Component | Quantity (mg) |
| --- | --- |
| Zolpidem Hemitartrate | 3.5 |
| Povidone K29/32 | 15.0 |
| Sodium Starch Glycolate (SSG) | 7.5 |
| Starch 1500 | 15.0 |
| Lactose Fast Flow | 82.0 |
| Prosolv SMCC 90 | 65.5 |
| Sodium bicarbonate | 40 |
| Magnesium Stearate | 1.5 |
| Total | 230 |

Manufacturing Process

Dispensing: Screen the zolpidem hemitartrate and excipients through screen #30. Dispense the required quantities of each ingredient.

Blending:
1. Transfer the zolpidem hemitartrate and Povidone K 29/32 to a V-Shell blender and blend for 2 min.
2. Add SSG and Starch 1500 to Step 1 and blend for another 2 min.
3. Add Lactose Fast Flow and Prosolv SMCC 90 to Step 2 and blend for another 10 min.
4. Mix an equal amount of the blend from Step 3 with magnesium stearate or sodium stearyl fumarate and transfer the mixture back to the V-Shell blender via screen # 30. Blend for 3 min.

Compression: Compress the final blend from Step 4 on a rotary press to a target tablet weight of 210 mg.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of treating middle-of-the-night insomnia in a non-elderly patient without prophylactically administering zolpidem, comprising:
dosing the patient with a pharmaceutical composition comprising about 0.5 to about 4.75 mg of zolpidem hemitartrate or a molar equivalent amount of a pharmaceutically acceptable form of zolpidem, wherein the pharmaceutical composition is substantially free of other hypnotic agents, wherein the patient awakens from sleep, and desires to resume sleep for less than 5 hours,
wherein the step of dosing the pharmaceutical composition is performed after the patient awakens from sleep, and
wherein the pharmaceutical composition permits the patient to awaken at a time about four hours after dosing without residual sedative effects.

2. The method of claim 1, wherein the patient resumes sleep within 30 minutes.

3. The method of claim 1, wherein about 50% of the maximum plasma concentration ($C_{max}$) of zolpidem is reached in the patient within about 30 minutes or less of dosing.

4. The method of claim 1, Wherein the pharmaceutical composition comprises about 3.0 mg to about 3.75 mg of zolpidem hemitartrate.

5. The method of claim 1, wherein the pharmaceutical composition provides delivery of zolpidem across the patient's oral mucosa.

6. The method of claim 1, wherein the pharmaceutically acceptable form of zolpidem is a salt form of zolpidem.

7. The method of claim 1, wherein the pharmaceutical composition further comprises sodium stearyl fumarate.

8. The method of claim 1, wherein the pharmaceutical composition comprises about 3.5 mg of zolpidem hemitartrate.

9. The method of claim 4, wherein the pharmaceutical composition provides delivery of zolpidem across the patient's oral mucosa.

10. The method of claim 8, wherein the pharmaceutical composition provides delivery of zolpidem across the patient's oral mucosa.

11. The method of claim 1, wherein the pharmaceutical composition is free of other hypnotic agents.

12. A method of treating middle-of-the-night insomnia in an elderly patient without prophylactically administering zolpidem, comprising:
dosing the patient with a pharmaceutical composition comprising about 1.5 to about 2.5 mg of zolpidem hemitartrate or a molar equivalent amount of a pharmaceutically acceptable form of zolpidem, wherein the pharmaceutical composition is substantially free of other hypnotic agents, wherein the patient awakens from sleep, and desires to resume sleep for less than 5 hours,
wherein the step of dosing the pharmaceutical composition is performed after the patient awakens from sleep, and
wherein the pharmaceutical composition permits the patient to awaken at a time about four hours after dosing without residual sedative effects.

13. The method of claim 12, wherein the patient resumes sleep within 30 minutes.

14. The method of claim 12, wherein about 50% of the maximum plasma concentration ($C_{max}$) of zolpidem is reached in the patient within about 30 minutes or less of dosing.

15. The method of claim 12, wherein the pharmaceutical composition provides delivery of zolpidem across the patient's oral mucosa.

16. The method of claim 12, wherein the pharmaceutically acceptable form of zolpidem is a salt form of zolpidem.

17. The method of claim 12, wherein the pharmaceutical composition further comprises sodium stearyl fumarate.

18. The method of claim 12, wherein the pharmaceutical composition comprises about 1.75 mg of zolpidem hemitartrate.

19. The of claim 18, wherein the pharmaceutical composition provides delivery of zolpidem across the patient's oral mucosa.

20. The method of claim 12, wherein the pharmaceutical composition is free of other hypnotic agents.

21. The method of claim 1, wherein the patient has a normal capacity to metabolize zolpidem.

22. The method of claim 1, wherein the pharmaceutical composition comprises about 3.5 mg of zolpidem hemitartrate, wherein the pharmaceutically acceptable form of zolpidem is a salt form of zolpidem, wherein the pharmaceutical composition is free of other hypnotic agents, wherein the pharmaceutical composition provides delivery of zolpidem across the patient's oral mucosa, and wherein the patient resumes sleep within 30 minutes.

23. The method of claim 22, wherein about 50% of the maximum plasma concentration ($C_{max}$) of zolpidem is reached in the patient within about 30 minutes or less of dosing.

24. The method of claim 12, wherein the pharmaceutical composition comprises about 1.75 mg of zolpidem hemitartrate, wherein the pharmaceutically acceptable form of zolpidem is a salt form of zolpidem, wherein the pharmaceutical composition is free of other hypnotic agents, wherein the pharmaceutical composition provides delivery of zolpidem across the patient's oral mucosa, and wherein the patient resumes sleep within 30 minutes.

25. The method of claim 24, wherein about 50% of the maximum plasma concentration ($C_{max}$) of zolpidem is reached in the patient within about 30 minutes or less of dosing.

* * * * *